(12) United States Patent  
Sundermeyer et al.

(10) Patent No.: US 7,328,625 B2  
(45) Date of Patent: Feb. 12, 2008

(54) SYSTEMS AND METHODS FOR DETERMINING FATIGUE LIFE

(75) Inventors: Jeffry Neil Sundermeyer, Dunlap, IL (US); Nitin R. Patel, Peoria, IL (US); Ryan Paul Allgaier, East Peoria, IL (US); Don Sit, Peoria, IL (US); Timothy Allen Vik, Sparland, IL (US); Jeffrey Dale Baskett, Peoria, IL (US); Hiroko Kyuba, Peoria, IL (US); Daniel Kimsey Dunn, III, Dunlap, IL (US); Byron Edwin Truax, Dunlap, IL (US); Burton Roland Clarke, Cuba, IL (US)

(73) Assignee: Caterpillar Inc., Peoria, IL (US)

( * ) Notice: Subject to any disclaimer, the term of this patent is extended or adjusted under 35 U.S.C. 154(b) by 201 days.

(21) Appl. No.: 11/227,157

(22) Filed: Sep. 16, 2005

(65) Prior Publication Data

US 2006/0243055 A1    Nov. 2, 2006

Related U.S. Application Data

(60) Provisional application No. 60/675,493, filed on Apr. 28, 2005.

(51) Int. Cl.  
*G01N 3/00* (2006.01)

(52) U.S. Cl. .................................................. 73/806

(58) Field of Classification Search ............... 73/799, 73/104, 40, 806; 428/76, 209, 156; 324/209  
See application file for complete search history.

(56) References Cited

U.S. PATENT DOCUMENTS

| 3,350,926 | A | 11/1967 | Webb |
|---|---|---|---|
| 4,280,363 | A | 7/1981 | Johansson |
| 4,336,595 | A | 6/1982 | Adams et al. |
| 4,412,456 | A | 11/1983 | Wilhelm et al. |
| 4,526,044 | A | 7/1985 | Moser et al. |
| 4,680,585 | A | 7/1987 | Fasching |

(Continued)

FOREIGN PATENT DOCUMENTS

EP    0 291 344    11/1988

(Continued)

OTHER PUBLICATIONS

Product Information Sheet, Micro Stress Analysis and Forecasted Endurance, MicroSAFE™, Invocon, Inc., Technology Profile Mar. 2004, available at www.invocon.com.

(Continued)

*Primary Examiner*—Jewel Thompson  
(74) *Attorney, Agent, or Firm*—Finnegan, Henderson, Farabow, Garrett & Dunner

(57) ABSTRACT

A method and method of estimating fatigue life of a structure is disclosed. In one embodiment, the method may include determining strain on the structure using a plurality of gauges positioned on the structure. The method may also include detecting a parameter of the structure with a plurality of sensors positioned on the structure. Further, the method includes converting the detected parameter and the determined strain to proportional loads acting on the structure and transforming the proportional loads to coordinate system data associated with the structure. Based on the coordinate system data, the fatigue life of the structure may be estimated.

21 Claims, 14 Drawing Sheets

U.S. PATENT DOCUMENTS

| | | |
|---|---|---|
| 4,738,135 A | 4/1988 | Cadwell et al. |
| 5,019,760 A | 5/1991 | Chu et al. |
| 5,019,814 A | 5/1991 | Biggs et al. |
| 5,041,976 A | 8/1991 | Marko et al. |
| 5,070,458 A | 12/1991 | Gilmore et al. |
| 5,184,516 A | 2/1993 | Blazic et al. |
| 5,284,062 A | 2/1994 | Ryffel |
| 5,353,645 A | 10/1994 | Feldman et al. |
| 5,402,689 A | 4/1995 | Grogan |
| 5,531,122 A | 7/1996 | Chatham et al. |
| 5,598,738 A | 2/1997 | Buescher, Jr. et al. |
| 5,684,254 A | 11/1997 | Nakazaki et al. |
| 5,723,779 A | 3/1998 | Hara et al. |
| 5,774,376 A | 6/1998 | Manning |
| 5,872,316 A | 2/1999 | Duggirala et al. |
| 5,970,393 A | 10/1999 | Khorrami et al. |
| 6,006,163 A | 12/1999 | Lichtenwalner et al. |
| 6,012,337 A | 1/2000 | Hodge |
| 6,014,896 A | 1/2000 | Schoess |
| 6,052,925 A | 4/2000 | Reiners |
| 6,076,405 A | 6/2000 | Schoess |
| 6,125,333 A | 9/2000 | Pun |
| 6,155,292 A | 12/2000 | Kurata |
| 6,181,841 B1 | 1/2001 | Hodge |
| 6,192,759 B1 | 2/2001 | Schoess |
| 6,292,108 B1 | 9/2001 | Straser et al. |
| 6,370,964 B1 | 4/2002 | Chang et al. |
| 6,396,262 B2 | 5/2002 | Light et al. |
| 6,433,629 B2 | 8/2002 | Hamel et al. |
| 6,476,377 B1 | 11/2002 | Hodge |
| 6,480,792 B1 | 11/2002 | Prendergast |
| 6,487,914 B1 | 12/2002 | Hodge |
| 6,499,368 B2 | 12/2002 | Arms et al. |
| 6,529,127 B2 | 3/2003 | Townsend et al. |
| 6,533,502 B2 | 3/2003 | McVay et al. |
| 6,556,288 B1 | 4/2003 | Chovan |
| 6,588,282 B2 | 7/2003 | Arms |
| 6,617,963 B1 | 9/2003 | Watters et al. |
| 6,622,567 B1 | 9/2003 | Hamel et al. |
| 6,647,161 B1 | 11/2003 | Hodge |
| 6,693,548 B2 | 2/2004 | Boyce et al. |
| 6,703,600 B1 | 3/2004 | Hodge |
| 6,714,763 B2 | 3/2004 | Hamel et al. |
| 6,718,268 B2 | 4/2004 | Fantana et al. |
| 6,768,065 B2 | 7/2004 | Bertenburg et al. |
| 6,768,312 B2 | 7/2004 | Sun et al. |
| 6,858,809 B2 | 2/2005 | Bender |
| 6,973,838 B2 | 12/2005 | Denis |
| 2002/0050925 A1 | 5/2002 | Arms et al. |
| 2002/0128751 A1 | 9/2002 | Engstrom et al. |
| 2002/0154029 A1 | 10/2002 | Watters |
| 2002/0190723 A1 | 12/2002 | Sun et al. |
| 2003/0009300 A1 | 1/2003 | Giurglutiu |
| 2003/0036891 A1 | 2/2003 | Aragones et al. |
| 2003/0071615 A1 | 4/2003 | Schlicker et al. |
| 2003/0093242 A1 | 5/2003 | Olsson |
| 2003/0164700 A1 | 9/2003 | Goldfine et al. |
| 2003/0173958 A1 | 9/2003 | Goldfine et al. |
| 2004/0025595 A1 | 2/2004 | Brennan |
| 2004/0078170 A1 | 4/2004 | Di Marzio |
| 2004/0078662 A1 | 4/2004 | Hamel et al. |
| 2004/0113790 A1 | 6/2004 | Hamel et al. |
| 2004/0122618 A1 | 6/2004 | Suzuki et al. |
| 2004/0153270 A1 | 8/2004 | Yamashita et al. |
| 2004/0204278 A1 | 10/2004 | Olsson |
| 2004/0260512 A1 | 12/2004 | Olsson |
| 2005/0017602 A1 | 1/2005 | Arms et al. |
| 2005/0021245 A1 | 1/2005 | Furuno et al. |
| 2005/0025176 A1 | 2/2005 | Ko et al. ............. 370/448 |
| 2005/0087235 A1 | 4/2005 | Skorpik et al. |
| 2005/0089425 A1 | 4/2005 | Boone et al. |
| 2005/0210340 A1 | 9/2005 | Townsend et al. |
| 2006/0017545 A1 | 1/2006 | Volpi et al. |
| 2006/0047232 A1 | 3/2006 | Bourne et al. |
| 2006/0243056 A1* | 11/2006 | Sundermeyer et al. ........ 73/760 |

FOREIGN PATENT DOCUMENTS

| | | |
|---|---|---|
| GB | 2 387 911 | 10/2003 |
| GB | 2 417 322 | 2/2006 |
| JP | 62194430 | 8/1987 |
| JP | 04042027 | 2/1992 |
| JP | 09236479 | 9/1997 |
| JP | 2005140653 | 6/2005 |
| WO | WO 03/008925 A1 | 1/2003 |

OTHER PUBLICATIONS

Product Information Sheet, Invocon, Inc., Technology Overview, MicroSAFE™, available at http://www.invocon.com/MicroSAFE_tech_overview.html.

X-33 Integrated Vehicle Health Monitoring (IVHM), Online, http://nesb.larc.nasa.qov/NESB/ndetasks/2000/x-33.html, visited Sep. 3, 2004.

PCT International Search Report mailed Nov. 8, 2006.

Allen et al, "A Structural Health Monitoring System for Earthmoving Machines," IEEE Conference on Electro Information Technology (EIT), May 2005 (5 pages).

Berger et al, "Consideration of Fracture Mechanics Analysis and Defects Dimension Measurement Assessment for the Trans-Alaska Oil Pipeline Girth Welds," vol. II, National Bureau of Standards, National Technical Information Service (NTIS), Dept. of Commerce, Oct. 18, 1976 (141 pages, front and back).

Fash (Ford Motor Co.), Modeling of Shock Absorber Behavior Using Artificial Neural Networks, SAE International, Mar. 17, 2004 (10 pages).

Gundersen et al, "The Use of an Integrated Multiple Neural Network Structure for Simultaneous Prediction of Weld Shape, Mechanical Properties, and Distortion in 6063-T6 and 6082-T6 Aluminum Assemblies," published in Ninth International Conference on Computer Technology in Welding, May 2000, pp. 255-300 (45 pages).

Polanco, "Estimation of Structural Component Loads in Helicopters: A Review of Current Methodologies," DSTO-TN-0239, Dec. 1999 (71 pages).

Sundermeyer et al, "SHIELD (Structural Health Integrated Electronic Life Determination)," Proceedings of the 5th International Workshop on Structural Health Monitoring, Sep. 2005 (13 pages).

Volvo Construction Equipment MATRIS, Ref. VOE21 B 1000351, 2004 (4 pages).

Jones, Jerry E., "Meeting in St. Louis on SHIELD IP Issues," electronic mail communication dated Nov. 9, 2005 (9 pages).

X-33 Integrated Vehicle Health Monitoring (IVHM), Online, http://nesb.larc.nasa.qov/NESB/ndetasks/2000/x-33.html, visited Sep. 3, 2004.

Khodja et al., Developement of Neural Networks module for fault identification in asynchronous machine using various types of references signals, 0-7803-9235, publish Aug. 24, 2005, IEEE, p. 537-542, and abstract showing publication info.

* cited by examiner

SYSTEMS AND METHODS FOR DETERMINING FATIGUE LIFE

CROSS REFERENCE TO RELATED APPLICATIONS

This application claims priority to and the benefit of the filing date of U.S. Provisional Patent Application No. 60/675,493, filed Apr. 28, 2005, which is herein incorporated by reference in its entirety.

Further, this application is related to U.S. Patent application Ser. No. 11/227,155, filed Sep. 16, 2005 entitled CLASSIFYING A WORK MACHINE OPERATION and U.S. Patent application Ser. No. 11/227,269, filed Sep. 16, 2005 entitled SYSTEMS AND METHODS FOR MAINTAINING LOAD HISTORIES, both of which are herein incorporated by reference in their entirety.

This invention was made with U.S. Government support under cooperative agreement No. 70NANB2H3064 awarded by the National Institute of Standards and Technology (NIST).

The U.S. Government has certain rights in the invention.

TECHNICAL FIELD

This disclosure relates generally to a system and method for monitoring, determining, and evaluating the loads, health, and use of a work machine.

BACKGROUND

A typical work machine, such as, for example, a tractor, dozer, loader, earth mover, or other such piece of equipment, may have any number of mechanical components and systems that are subject to fatigue damage which could lead to structural failures. One method for monitoring fatigue damage on a work machine structure is to perform a manual, visual inspection. However, such a method may be impractical for several reasons. First, such an inspection may not be as comprehensive as desired. This may be due, in part, to the difficulty in accessing some components of the work machine, such as when the structure in question is concealed and cannot be viewed without dismantling a portion of the work machine. Second, a manual inspection of structural systems can only be performed on a periodic basis, yet damage and resulting catastrophic failure still can occur between inspections. Third, a manual inspection may not be able to detect how much fatigue damage may have already occurred in the work machine, or predict the mean time till failure of one or more machine components based on the fatigue damage. While manual inspection may provide some insight into damage that is visible to an inspector, (e.g., large visible cracks in a machine component), internal damage may not be readily apparent through manual inspection (e.g., small internal cracks in a component).

Some systems have been proposed utilizing various ways of monitoring structures electronically to detect fatigue damage. However, these proposed systems have not adequately addressed the monitoring of structures with rapidly changing load pictures, such as movable work machines. This is due in part to the way these proposed systems collect data about the structure. These proposed systems may collect data about the structure at a relatively low sampling rate to ease the computing burden of performing analysis on the data and storing the analysis results. However, a low sampling rate may entirely miss some load states which endure very briefly.

Many critical load states experienced by a work machine may only endure very briefly. For example, when a wheel loader is digging and the bucket hits a rock, the load state may peak for a few brief moments before the rock is broken or dug out. In structures with rapidly changing load states, the sampling rate must be high in order to capture these peak load states which may endure only very briefly. If the sampling rate is too slow to "see" all or most of these critical load states, the analysis results will not accurately reflect the true condition of the structure.

However, for a complex structure rapid sampling rates may present an enormous challenge as the computing power required to analyze the rapidly sampled data in the traditional manner could be unachievable.

Another proposed system for monitoring the structural integrity of a structure is disclosed in U.S. Pat. No. 5,774,376 to Manning. The '376 patent discloses a system for monitoring the structural integrity of a mechanical structure utilizing a neural network to analyze data and characterize the structure's health. In use, a sensor attached to the mechanical structure senses vibrations and generates an output signal based on the vibrations. The sensor output signal is sent through control electronics to a neural network that generates an output that characterizes the structural integrity of the mechanical structure. However, the system disclosed in the '376 patent is subject to a number of shortcomings. Experimental results in the literature have suggested that changes in vibration signals that result from the presence of cracks are small unless the crack has already grown to a considerable size. The use of vibrations as an input also suggests that the structure must be excited with frequency content that at least partially activates one of the natural modes of the structure. Many structures never receive such input during normal operation, which would require that the excitation be delivered in some artificial manner, which could be cumbersome or impossible. Furthermore, the '376 patent provides a means of damage detection only. It does not provide any information on the usage habits or loading that would have been the underlying cause of that damage.

SUMMARY OF THE INVENTION

A method and method of estimating fatigue life of a structure is disclosed. In one embodiment, the method may include determining strain on the structure using a plurality of gauges positioned on the structure. The method may also include detecting a parameter of the structure with a plurality of sensors positioned on the structure. Further, the method includes converting the detected parameter and the determined strain to proportional loads acting on the structure and transforming the proportional loads to coordinate system data associated with the structure. Based on the coordinate system data, the fatigue life of the structure may be estimated.

In another embodiment, a system for estimating fatigue life of a structure is disclosed that may include a structure positioned on a work machine performing operations. Further, the system may include gauges positioned on the structure and configured to measure strain on the structure during operations of the work machine. Also, sensors may be positioned on the structure that are configured to detect a parameter associated with the structure. The system may also include a computer located on the work machine. The computer may be configured to determine strain on the structure based on the measured strain, convert the detected parameter and the determined strain to proportional loads acting on the structure, transform the proportional loads to a coordinate system data associated with the structure, and estimate a fatigue life of the structure based on the coordinate system data.

DETAILED DESCRIPTION

Figure 1:
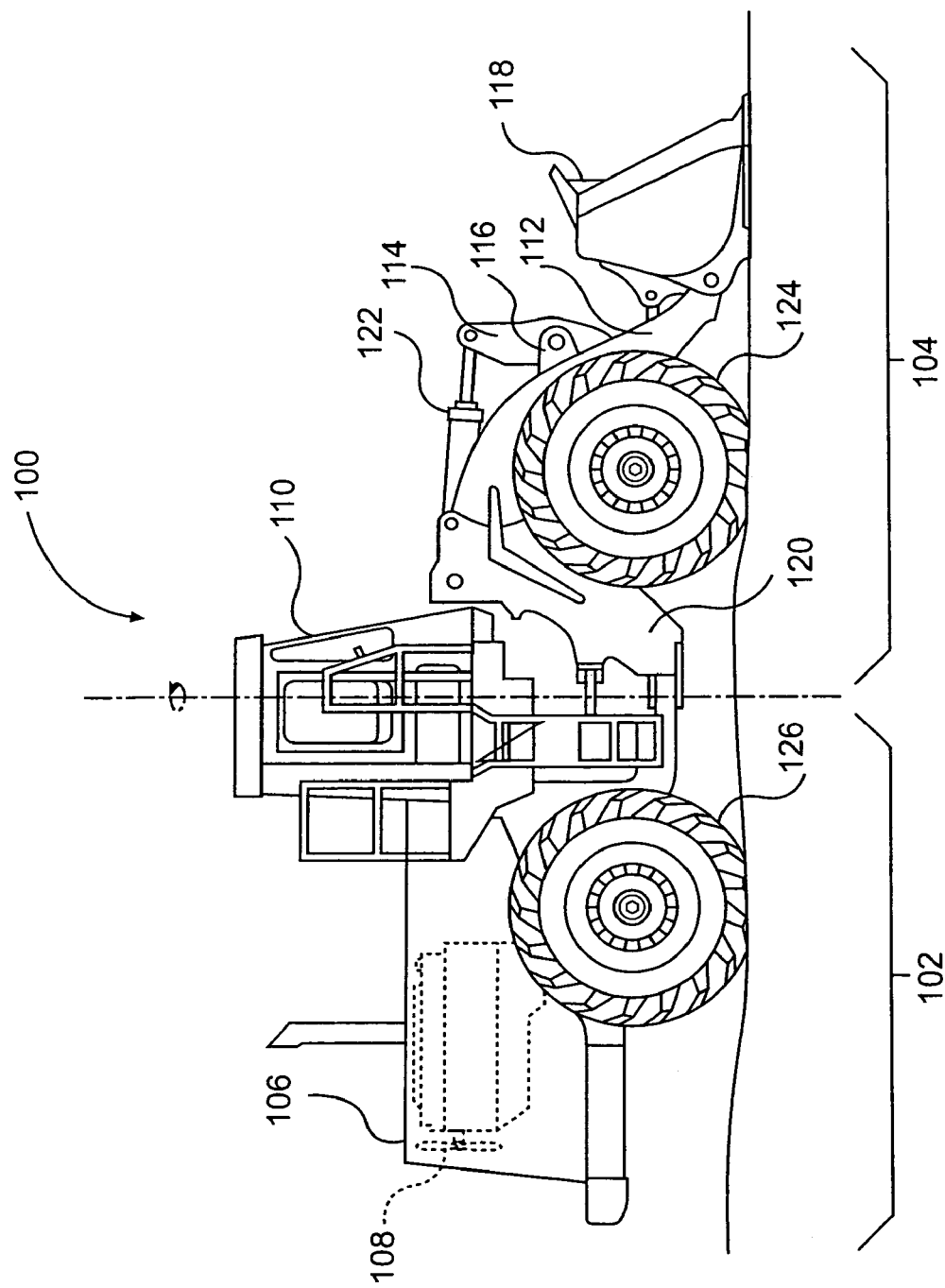
FIG. 1 is a diagrammatic illustration of an exemplary work machine consistent with certain disclosed embodiments.

Reference will now be made in detail to exemplary embodiments and illustrations. Wherever possible, the same reference numbers will be used throughout the drawings to refer to the same or like parts. While specific configurations and arrangements are discussed, it should be understood that this is done for illustrative purposes only.

Methods and systems consistent with the disclosed embodiments perform processes that determine, among other things, loads, health, and use of a work machine or components of a work machine. In one embodiment, a work machine may be outfitted with a number of sensors. Some of the sensors may measure information reflecting the orientation and movement of the work machine, such as inclination relative to the ground, and the positions of the movable parts of the machine. Other sensors may measure information about forces acting on the work machine. Additional sensors may also measure the strain experienced by certain components of the machine.

Certain forces acting on the work machine, however, may be difficult to directly measure using these sensors, such as ground engaging forces acting on the machine's wheels. The disclosed embodiments overcome this problem by using the measured forces and strains, along with other information, such as orientation information, to determine unmeasured forces. The unmeasured forces may be calculated using, for example, traditional Newtonian force balance and stress-strain calculations. Moreover, in certain embodiments, a neural network may be used to more quickly solve for these unknown forces.

Accordingly, the type of data used and determined in certain disclosed embodiments may include different types of data. One type may be measured data associated with raw measured information reflecting forces experienced by a component or structure (e.g., pressure in a cylinder, etc.). A second type of data may be measured strain data associated with actual strains experienced by a component or structure. For example, sensors on opposite ends of a component may provide measured information that reflect the strain experienced by that component. Collectively, the first and second types of data may define the constraints of the state of a given body (e.g., a component, set of components, the entire work machine, etc.). Another type of data may include the unknown load data calculated using the measured data.

Once the measured forces are measured, and the unmeasured forces are calculated, methods and systems consistent with certain embodiments may generate a complete free body diagram of a portion (e.g., one or more components) or the entire work machine. Based on the complete free body diagram and the orientation data associated with the work machine, or a component thereof, the strain at any desired point on the work machine may be calculated. In certain embodiments where technology is used to obtain a fast sampling rate of the free body diagram, the calculated strain at a given point on the work machine may be used to continuously update a prediction of the remaining fatigue life of a structure surrounding the given point.

In certain embodiments, the data used in determining the remaining fatigue life of a work machine may be used for other purposes. For example, the data associated with the complete free body diagram, and other data reflecting the orientation and movement of the work machine, may be used to classify an operation of the work machine at any given point in time into one of several discrete operating states. For example, the data may be used to determine whether the work machine is digging or roading at any given point in time. As another example, the data of the free body diagram may be used to compute the weight of material in a bucket of the work machine following a digging operation. As another example, the data of the free body diagram and the orientation data, along with information reflecting the current position of the work machine's center of gravity at a given point in time or operation may be used to determined whether the work machine is in danger of tipping. In another example, the data of the free body diagram may be used to determine historically high loading states of the work machine, or individual components thereof, that are experienced during actual operation. The historical high loading state data may be used to better understand the forces experienced by the work machine, or components thereof, to assist in the design or manufacture stages associated with the machine. It should be noted that the above examples are not intended to be limiting, as there are many uses for using the data collected and calculated by the methods and systems disclosed herein.

Exemplary Work Machine

FIG. 1 shows an exemplary work machine 100 that may incorporate an electronic health monitoring system as disclosed herein. Work machine, as the term is used herein, refers to a fixed or mobile machine that performs some type of operation associated with a particular industry, such as mining, construction, farming, etc. and operates between or within work environments (e.g., construction site, mine site, power plants, etc.). A non-limiting example of a fixed machine includes an engine system operating in a plant or off-shore environment (e.g., off-shore drilling platform). Non-limiting examples of mobile machines include commercial machines, such as trucks, cranes, earth moving vehicles, mining vehicles, backhoes, material handling equipment, farming equipment, marine vessels, aircraft, and any type of movable machine that operates in a work environment. As shown in FIG. 1, work machines 100 is an earth moving type work machine. The type of work machine illustrated in FIG. 1 is exemplary and not intended to be limiting. It is contemplated that the disclosed embodiments may implement any type of work machine.

The exemplary work machine 100 may include a rear end 102 and a front end 104. The rear end may include an engine housing 106 and an operator station 110. The front end 104 may include one or more lift arms 112, one or more tilt levers 114, one or more tilt links 116, a work implement 118, and a non-engine end frame 120. In the example of work machine 100 being a wheel loader, work implement 118 is powered and controlled by a number of actuators, including a tilt actuator 122 and a lift actuator (not shown).

Work machine 100 may include front and rear ground engaging devices, such as front wheels 124 and rear wheels 126 that support work machine 100. The engine housing 106 may include a power source, such as an engine 108, that may provide power to the front and/or rear wheels 124, 126.

To control work machine 100, including work implement 118, an operator may manipulate one or more input devices that may be housed within the operator station 110. The input devices may ultimately control work machine 100 by extending and retracting hydraulic steering actuators, the tilt actuator 122, the lift actuator, and controlling engine 108. Although the health monitoring system is discussed with reference to a wheel loader, the principles and systems described herein are equally applicable to any work machine that may be used to perform a task.

Exemplary Monitoring System

Figure 2:
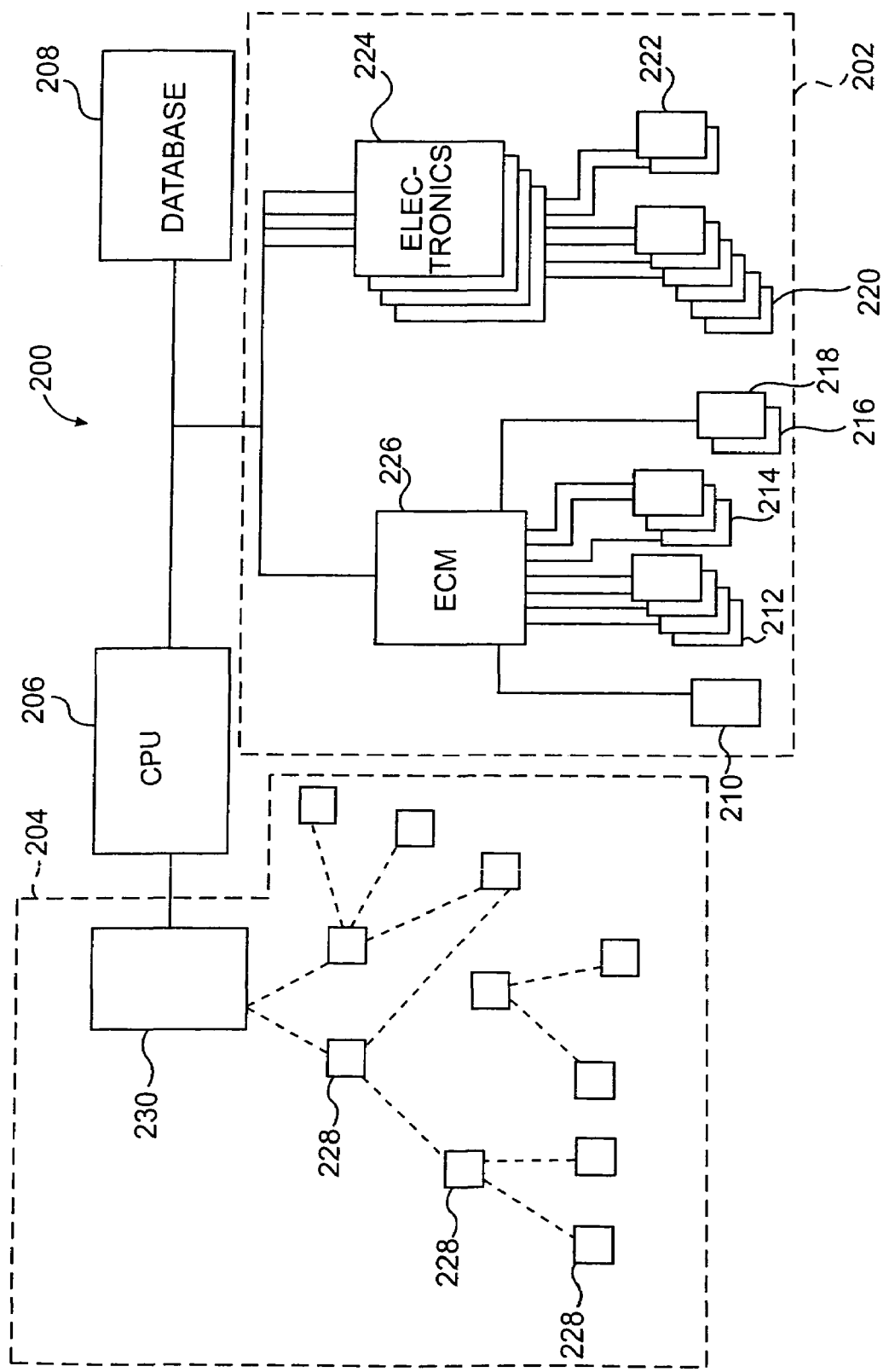
FIG. 2 is a block diagram of an exemplary monitoring system consistent with certain disclosed embodiments.

FIG. 2 shows an exemplary monitoring system 200 consistent with certain disclosed embodiments. In one embodiment, monitoring system 200 may be implemented on a work machine that has moving parts, a rapidly changing load state, etc., such as work machine 100. Further, monitoring system 200 may be configured to perform health and usage monitoring functions associated with the operations of work machine 100. That is, monitoring system 200 may be configured to process information affiliated with the dynamic load changes experienced by machine 100. Further, monitoring system 200 may be configured with hardware and/or software that enables it to process work machine-related data in real time, as well as generate, store, and manage information related to raw data obtained from one or more machine components, such as sensors. In this regard, the monitoring system may maintain a manageable set of information for analysis and reporting. Moreover, monitoring system 200 may include wireless communication elements that enable moving and non-moving components of work machine 100 to communicate without wired data links. Other aspects may be implemented by the disclosed embodiments and the configuration of monitoring system 200 is not limited to the examples listed above or described below.

Sensor Network

In the exemplary embodiment shown, the system 200 includes a wired sensor network 202, a wireless sensor network 204, a central computer 206 (which may be a digital signal processor (DSP)), and a memory component, such as a vehicle database 208. Wired sensor network 202 and wireless sensor network 204, together may include sensors for detecting, for example, hydraulic pressures in actuators, positions of cylinder rods, implement linkage angles, velocities and accelerations, steering articulation angle, strain on bolts forming structural joints, vehicle ground speed, inclination relative to the Earth, and forces on instrumented pins in linkages and other structures. Data obtained by wired sensor network 202 and wireless sensor network 204 may be used to perform structural health and usage monitoring.

The sensor networks 202 and 204 may each be configured to collect data indicative of loads acting on work machine 100. Although FIG. 2 shows a wired sensor network 202 and wireless sensor network 204, either network may be implemented as a wireless or wired network. In one example, wired sensor network 202 may include an orientation sensor 210, one or more hydraulic pressure sensors 212, one or more cylinder position sensors 214, one or more work implement position sensors 216, one or more work implement velocity sensors 218, load pins 220, and bending bridges 222. Generally, these may all be referred to as "sensors." In addition, wired sensor network 202 may include interface electronics 224 and/or an electronic control module (ECM) 226. In other embodiments, wired sensor network 202 of the exemplary health and usage monitoring system 200 may include additional sensors and/or different sensors or other components.

In general, the sensors implemented by work machine 100 (e.g., sensors 210-228) may be separated into three categories: sensors that sense orientation and movement of the machine, sensors that measure loads (e.g., cylinder pressure sensors, strain gauges on the rod ends of hydraulic cylinders, etc.), and sensors that sense strain at some point, such as a sensor on a structural frame within work machine 100. The number and position of the sensors implemented within work machine 100 may depend on the type of work machine, the type of component(s) within work machine, the desired and actual use of the machine, and other factors. For example, a certain number of sensors associated with the first two categories may be selectively positioned in order to provide adequate information to constrain the problem of generating the entire free body diagram of the machine or machine component. The sensors from the third group, however, may be positioned in locations to provide a base set of measured data to compare to calculated strains (e.g., normal strain values). Further, based on the location of certain machine components, or other sensors, a sensor positioned on these certain machine components may be wired or wireless.

Orientation sensor 210 may be one or more inclinometers disposed on work machine 100 to measure one or both of pitch and roll of work machine 100 relative to the Earth. Hydraulic pressure sensors 212 may be associated with a hydraulic system to detect fluid pressure. In one exemplary embodiment, pressure sensors 212 may be associated with a cylinder head of a hydraulic actuator, such as the tilt actuator 122. Hydraulic pressure sensors 212 may be disposed at other locations about work machine 100 to measure hydraulic pressures. Pressure sensors 212 may provide information regarding one or more forces acting on the structure of work machine 100 at connection points of the hydraulic actuator.

Cylinder position sensors 214 may be configured to sense the movement and relative position of one or more components of work machine 100, such as components of front end 104. Position sensors 214 may be operatively coupled, for example, to actuators, such as tilt actuator 122. Alternatively, position sensors 214 may be operatively coupled to the joints connecting the various components of front end 104. Some examples of suitable position sensors 214 include, among others, length potentiometers, radio frequency resonance sensors, rotary potentiometers, machine articulation angle sensors and the like.

Work implement position sensors 216 may be associated with work implement 118 in a manner to detect its position. In one exemplary embodiment, work implement position sensors 216 are rotary position sensors disposed at pin connections on work implement 118. Other position sensors also may be used including, among others, radio frequency resonance sensors, rotary potentiometers, angle position sensors, and the like. Work implement acceleration sensors 218 may include an accelerometer or other type of sensor or sensors configured to monitor acceleration and may be associated with work implement 118 in a manner to properly detect acceleration of any desired point. Velocities may also be obtained based on the time-derivative of position sensors for the bucket or other similar component of work machine 100.

Load pins 220 may be configured to measure force in x and y-axes in inner and outer shear planes of a pin and may be instrumented with, for example, one or more strain gauges. The load pins 220 could be instrumented with strain gauges on the outer or inner surface of the pin, or they could be instrumented with some other technology designed to react to the stress state in the pin, such as magnetostriction. Load pins 220 may be disposed at joints on work machine 100. In one exemplary embodiment, load pins 220 are disposed at joints connecting components of work implement 118 and/or connecting the actuators, such as tilt actuator 122, to work implement 118. Load pins 220 may be disposed at other joints about work machine 100.

Bending bridges 222 may be configured to measure strain in or along surfaces, such as, for example, along sides of lift arm 112. In one exemplary embodiment, the bending bridges may include, for example, four strain gauges. In one exemplary embodiment, the strain gauges on bending bridges 222 may be configured to provide one combined output.

Interface electronics 224 may be in communication with the sensors, such as load pins 220 and bending bridges 222, and may be configured to receive data signals from the sensors, process the data signals, and communicate data to computer 206. Interface electronics 224 may include, for example, a module including, for example, a PIC18F 258 microprocessor, 32 KB Flash, 1.5 KB RAM, 256 bytes EEPROM, CAN 2.0B interface with 12 bit external A/D sampling, and 4 strain channels. In one exemplary embodiment, health and usage monitoring system 200 may include nine interface electronics 224, each associated with load pins 220 and bending bridges 222. The interface electronics may be configured to communicate time-stamped and synchronized information, along with sensed values.

Electronic control module (ECM) 226 may contain a processor and a memory device, and may be configured to receive data signals from sensors 210, 212, 214, 216, 218, process the data signals, and communicate data to computer 206. The processor in ECM 226 may be a microprocessor or other processor, and may be configured to execute computer readable code or computer programming to perform functions, as is known in the art. The memory device in the ECM 226 may be in communication with the processor, and may provide storage of computer programs and executable code, including algorithms and data enabling processing of the data received from sensors 210, 212, 214, 216, 218. In one exemplary embodiment, ECM 226 may include a MPC555 microprocessor, 2 MB ROM, 256 KB RAM, and 32 KB EEPROM.

Figure 3:
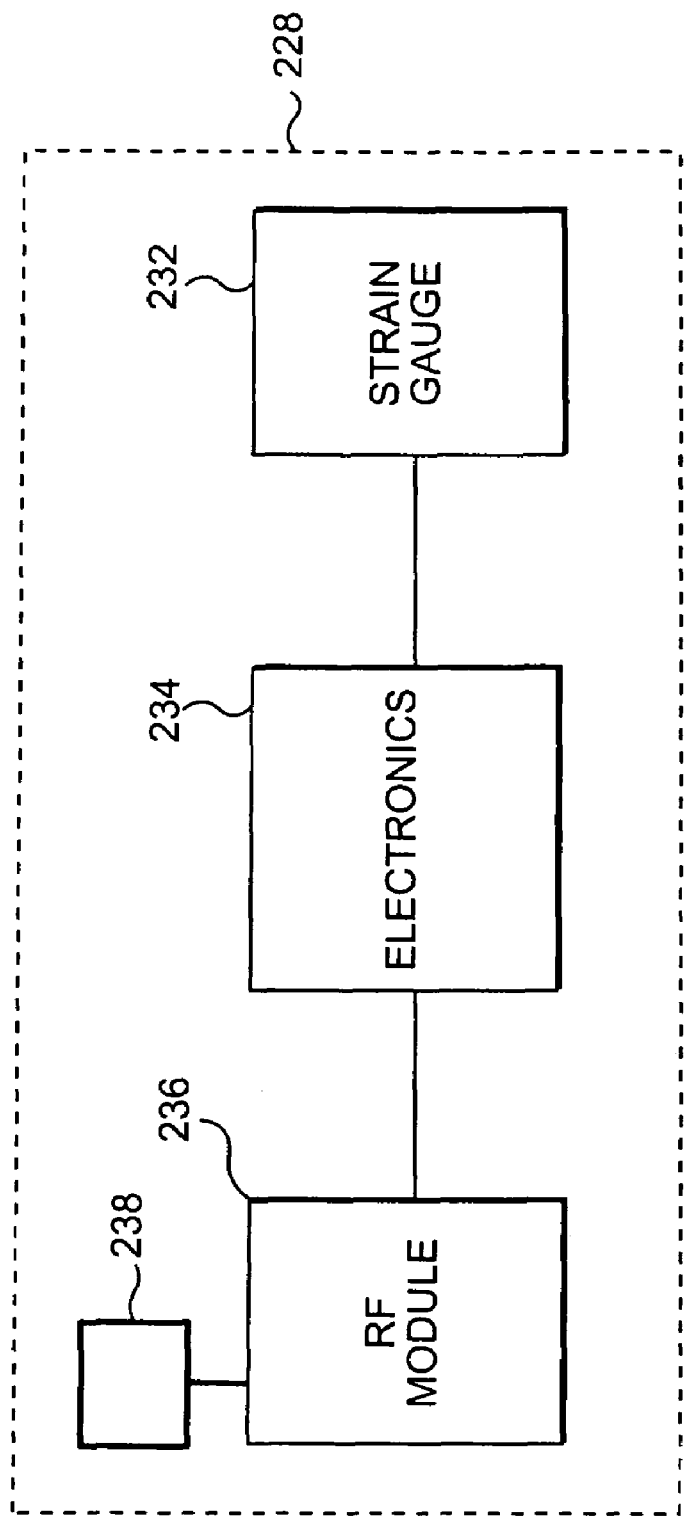
FIG. 3 is a block diagram of an exemplary wireless node consistent with certain disclosed embodiments.

Wireless sensor network 204 may include a number of wireless nodes 228 and a gateway node 230. Wireless nodes 228 may be disposed about work machine 100 and may be configured to communicate data signals representative of measured strain to other wireless nodes, and ultimately to gateway node 230. One exemplary wireless node 228 is shown in FIG. 3. The wireless node 228 may include one or more strain gauges 232, conditioning electronics 234, an RF module 236, and a transceiver 238. Strain gauges 232 may be configured to measure local strain on a component of work machine 100. In one exemplary embodiment, strain gauges 232 may include a rosette providing three sets of strain data from multiple strain gauges so that the strain tensor may be completely defined at each sensed point of a machine 100. Electronics 234 may process or filter a signal representative of the strain from strain gauges 232 and may communicate data representative of the strain to RF module 236, which may communicate the data to other wireless nodes 228 and/or to gateway node 230 using transceiver 238. It should be noted that wireless node 228 in FIG. 3 is exemplary only, and may be configured in any known manner. In one exemplary embodiment, wireless node 228 may include a receiver or a transmitter instead of transceiver 238. In another exemplary embodiment, wireless nodes 228 may each include a processor and memory for processing signals from strain gauges 232. Wireless nodes 228 may include other components, including a power source, such as a battery. Other configurations would be apparent to one skilled in the art.

In one exemplary embodiment, measurements from wireless nodes 228 may be tagged with timestamps to allow computer 206 to synchronize the measurements from the different nodes and from the wired sensor network 202. In one exemplary embodiment, wireless nodes 228 may concatenate measurements over relatively long periods before data transmission. Means for synchronizing the measurements may be incorporated into the transmitted data.

To minimize power usage, wireless nodes 228 may compress and accumulate their data and then send the accumulated data periodically, over a programmable time interval. In one exemplary embodiment, wireless nodes 228 are programmed to send their accumulated strain data over two second intervals. This means that computer 206, in addition to scaling the sensor data, may rebuild the time history of the actual strains.

The gateway node 230 may be in communication with wireless nodes 228 and may be in communication with computer 206. Accordingly, the gateway node 230 may be configured to communicate data indicative of the strain collected by wireless nodes 228 to computer 206.

It should be noted that the health and usage monitoring system 200 also may be operable with a single wired network or a single wireless network, rather than simultaneously employing a wired and a wireless network. Further, the number of gauges and other instruments used to collect data may vary depending upon the application and type of work machine 100.

Computer 206 may be in communication with the gateway node 230, the ECM 226, and the interface electronics 224. Computer 206 may be configured to receive data signals, process the data signals, and communicate data to the vehicle database 208. Computer 206 may be one or more processors configured to execute computer readable code that perform processes consistent with certain disclosed embodiments, such as functions to determine the life of or load on one or more components of work machine 100. In one exemplary embodiment, computer 206 may be associated with a data transfer device (not shown) that may provide output of data from computer 206 and/or vehicle database 208. The data transfer device could be a port connectable to a service tool, such as a laptop computer, a hand-held data device, and a wireless transmitter, among others. Computer 206 may include, for example, resources to process varying numbers of inputs. For instance, computer 206 may execute program code that stores data in a first-in-first-out buffer at maximum expected input sampling rates. Additionally, computer 206 may be configured to perform algorithms consistent with the health and usage monitoring embodiments disclosed herein, such as processing data through one or more neural networks, performing floating-point matrix calculations, etc. In one exemplary embodiment, computer 206 may be an MPC5200 type processor using a QNX real-time operating system.

Vehicle database 208 may include one or more memory devices that store data and computer programs and/or executable code, including algorithms and data enabling processing of the data received from gateway node 230, ECM 226, and interface electronics 224. The memory devices may be any type of memory device(s) known in the art that is compatible with computer 206. Vehicle database 208 also may be configured to store data calculated by computer 206 and may be configured to store computer programs and other information accessible by computer 206.

In one embodiment, database 208 may store neural network software that, when executed by computer 206, performs neural network processes consistent with the disclosed embodiments. A neural network is designed to mimic the operations of the human brain by determining the interaction between input and response variables based on a network of processing cells. The cells, commonly known as neurons or nodes, are generally arranged in layers, with each cell receiving inputs from a preceding layer and providing an output to a subsequent layer. The interconnections or links that-transfer the inputs and outputs in a neural network are associated with a weight value that may be adjusted to allow the network to produce a predicted output value. Neural networks may provide predicted response values based on historical data associated with modeled data provided as independent input variables to the network. Neural networks may be trained by adjusting the data values associated with the weights of the network each time the historical data is provided as an input to allow the network to accurately predict the output variables. To do so, the predicted outputs are compared to actual response data of the system and weights are adjusted accordingly until a target response value is obtained.

Overview Process

Figure 4:
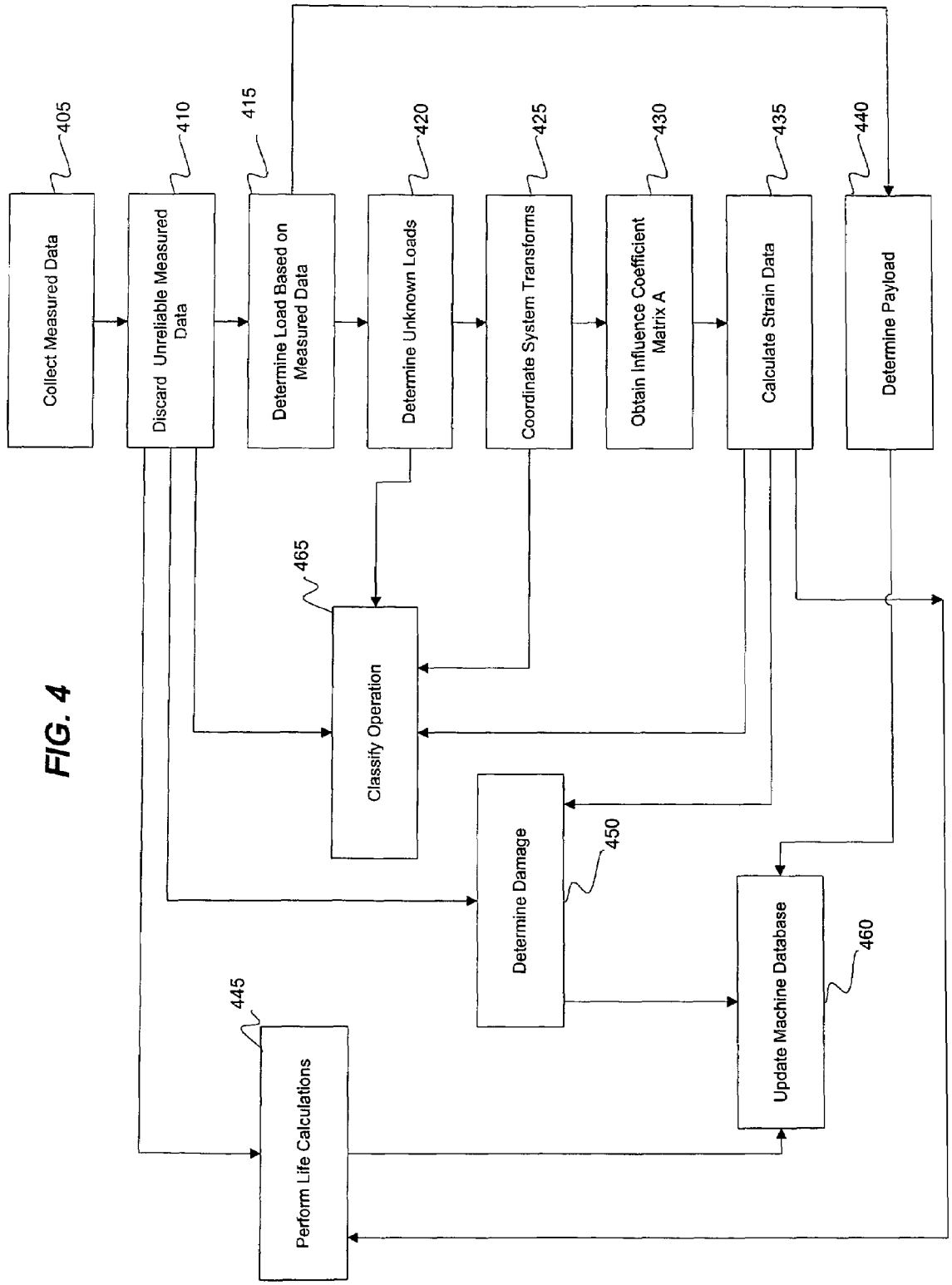
FIG. 4 is a summary flow chart of exemplary processes performed by methods and systems consistent with certain disclosed embodiments.

As explained, methods and systems consistent with the disclosed embodiments collect, determine, and analyze data associated with forces experienced by work machine 100. Based on the data, embodiments may calculate unknown variables, such as unknown loads, classify work machine operations, generate free body diagrams, calculate strains, determine the life of a component(s) of work machine 100, and evaluate and predict the life of component(s) of work machine 100 or of machine 100 itself. FIG. 4 shows a flowchart summarizing some exemplary processes that may be performed by methods and systems consistent with certain disclosed embodiments.

Initially, in one embodiment, work machine 100 may experience a startup stage that may include powering up work machine 100 or otherwise activating monitoring system 200. At startup, computer 206 may send one or more signals to "wake up" wireless nodes 228. Sending the signal may include activating or commanding an intermediary component to route the wake up signal to other connected components. For example, computer 206 may issue an activation signal to gateway node 230 or a first wireless node 228, which in turn notifies one or more remaining wireless nodes 228 to awake and begin processing. At the same time, or at a different time, computer 206 may communicate a signal to one or more wired sensors 210-222 in a similar manner as described above, to begin collecting and processing inputs.

Once awakened, one or more of sensors 210, 212, 214, 216, 218, 220, 222, 228 (hereinafter collectively referred to as "sensors 210-228") may collect raw measured data from their associated components (Step 405). For example, sensors 210-228 may be disposed in different locations on front end 104 of work machine 100 to measure one or more parameters of lift arm 112, tilt lever 114, tilt link 116, work implement 118, and/or non-engine end frame 120. Once obtained, the raw measured data may be time-stamped and communicated to computer 206 for subsequent processing.

In one embodiment, computer 206 may determine whether the data received from each sensor is reliable. In one exemplary embodiment, computer 206 may determine data reliability executing neural network software configured to recognize reliable and unreliable data for each of the types of data received from sensors 210-228. For example, the neural network executed by computer 206 may receive as input data from a sensor showing a flatline channel. Based on predetermined configurations, the neural network may recognize the flatline channel as an indicator that the particular sensor has ceased functioning properly, and therefore, its data may be unreliable. In another example, the neural network may receive sensor data that is determined to include a certain threshold of reliable data (e.g., a majority of data). For example, the neural network may recognize that a majority of a sensor's data is reliable, but also includes an occasional outlier of incorrect data. The neural network may recognize this outlier as unreliable data. Therefore, based on an analysis of the data itself, the neural network may classify the data as either reliable or unreliable.

In other exemplary embodiments, computer 206 may use other processes to determine whether the data is reliable. For example, in one exemplary embodiment, computer 206 may perform a logic-based process that monitors the first and second time-derivatives of the incoming data signals. In this embodiment, the flatline channel may have a zero first derivative at all times, and therefore, may be identified as unreliable. In addition, an otherwise correctly functioning channel with an occasional noise spike may have unusually large higher derivatives at the times associated with the noise spike. Therefore, again, the noise spike may be identified as unreliable.

If computer 206 determines the raw measured data to be unreliable, the unreliable data may be discarded and substituted with a data determined using interpolation techniques known in the art (Step 410). Alternatively, when the unreliable data is a strain measurement for a particular component of machine 100, the unreliable strain measurement may be substituted with a previously calculated strain for that component. In some exemplary embodiments, the unreliable data is discarded and the strain calculation process continues without substituting calculated data. In other exemplary embodiments, the processing iteration is suspended due to the unreliable data, and computer 206 resumes the strain calculation process at step 405. In other exemplary embodiments, other components of machine 100 may screen the measured data for reliability, such as gateway node 230, ECM 226, electronics 224, and/or at any of sensors 210-228. In these embodiments, the gateway node 230, the ECM 226, the electronics 224, and/or the sensors 210-228 may be configured with hardware and/or software that is capable of detecting unreliable measured data.

Also, in step 410, computer 206 may determine that measured strain data is included in the measured data collected in step 405. In certain embodiments, computer 206 may determine measured strain data based on collected measured data. For example, based on sensor data collected from sensors positioned on opposing sides of a machine component, computer 206 may determine the strain imposed on the component, or a portion thereof. Thus, in step 410, computer 206 may produce measured data of a first category (i.e., raw measured data reflecting forces on a particular component, such as pressure, etc.) and measured data of the second category (e.g., measured strain data).

In one embodiment, based on the measured data provided in Step 410, computer 206 may determine the load(s) on various structural bodies within work machine 100 (e.g., one or more components of work machine 100) (Step 415). Computer 206 may use the load data to determine the strain and fatigue life associated with one or more monitored components of work machine 100, as described further below. In calculating the load(s), computer 206 may convert the measured strain into a proportional quantity that reflects information that is more relevant to the actual physical strain values on the measured component than the measured strain data provided in step 410. For example, computer 206 may convert the measured raw strain data associated with an instrumented pin located on a machine component into data representing the resultant load and local moments for the pin. In another example, computer 206 may convert measured axial strain data for a cylinder rod to load-based data, which may be then shifted in order to match load data calculated from head-end and rod-end pressure readings associated with the cylinder rod. In this example, a strain gauge may measure strain data for the cylinder. The strain gauge may provide the measured strain data to computer 206 for determining the load applied to the cylinder when it is "bottomed-out" (i.e., when a rod within the cylinder is fully extended, thus forcing the piston to the edge of one end of the cylinder). In certain embodiments, computer 206 may shift received strain data to a corrected value. Because strain gauges may sense only strain relative to the time when the gauge was activated (i.e., turned on and operational), computer 206 may execute software that performs a linear regression analysis, or similar type of analysis, on the strain data to create a best-fit expression that is used to offset the loads calculated from the rod strain so that they are in agreement with loads calculated from cylinder pressures when the cylinder is not at either of the extreme limits of displacement. The linear regression techniques performed by computer 206 may be those techniques known in the art.

Also, in addition to cylinder forces, strain gauges may be implemented within work machine 100 that measure the axial force in tilt link 116. In this example, computer 206 may execute software that converts the measured strain data obtained from the strain gauge for tilt link 116 to load-based data using strain to force conversion methods known in the art. In instances where the strain gauge does not measure absolute strain data values, computer 206 may perform correction processes that correct the measured load on tilt link 116 to represent an absolute strain value. Computer 206 may then use linear regression analysis, or similar processes, to determine the axial load in tilt link 116.

In certain embodiments, tilt link 116 may experience a dump stop event during operation of work machine 100. A dump stop event is a condition when tilt link 116 impacts lift arm 112 during operation. The forces imposed on these elements during such an event may cause fluctuations in determining the load associated with tilt link 116. As such, computer 206 may execute processes that compensate for the forces occurring during a dump stop event to accurately determine the load experienced by tilt link 116. One process may be configured to provide an estimate of the load of tilt link 116 for non-dump stop event states (e.g., when the tilt lever 114 is not in contact with the lift arm 112). A second process may be configured to calculate tilt link 116 load during times when the tilt lever 114 is in contact with the lift arm 112. Each of these processes may be based on load determining algorithms and techniques known in the art and executed by computer 206.

In certain embodiments, one or more wireless strain gauges may be employed to measure the load on a given component of work machine 100. For instance, a wireless node 228 may be configured as a wireless strain gauge for tilt lever 114 that measures its tilt link load. It should be noted that such determinations may be performed using well-known kinematic equations. Further, to conserve the energy of wireless node 228, each node may be configured with a "sleep" mode. For instance, a wireless tilt lever 114 strain gauge, and its accompanying wireless node 228, may be placed in a low power mode (i.e., "sleep" mode) whenever the tilt lever 114 is not in contact with the lift arm 112. In another exemplary embodiment, computer 206 may estimate the load on a given machine component using a neural network configured to provide the output load based on known neural network programming software processes. It should be noted that component loads may be determined using other configurations and techniques, and the disclosed embodiments are not limited to the above described examples.

Computer 206 may also determine unknown loads (e.g., unmeasured loads) acting on or within work machine 100, such as all unknown loads for the entire machine, or certain portions of machine 100, such as a front section, lift arms, etc. For example, unknown loads may be associated with ground interface loads that cannot be measured directly by a sensor. In certain embodiments, computer 206 may determine unknown loads using a neural network or by employing traditional deterministic software based upon the equations of motion. Embodiments involving a neural network are described further below. In some applications, it may not be necessary to employ a neural network to determine the unknown loads. In certain embodiments, if inertial loading and contributions from mechanical vibration are not significant, computer 206 may use the Newtonian equations of static equilibrium to determine the unknown loads.

Once computer 206 determines the unknown loads, it may execute software that coordinates system transforms to associate all of the determined loads (known and unknown) to coordinate data corresponding to one or more respective components of work machine 100 (Step 425). This process allows computer 206 to generate a free-body diagram of one or more, or all of the respective components of work machine 100, which is described in further detail below in connection with FIG. 5.

As explained, the data collected and calculated by monitoring system 200 may be used to perform one or more processes consistent with certain disclosed embodiments. In one embodiment, the determined load data may be used to calculate strains experienced by one or more components of work machine 100. For instance, in one embodiment, computer 206 may obtain an influence coefficient matrix (A) that is stored in a memory device within work machine 100 (Step 430). The influence coefficient matrix (A) includes data reflecting the strain response at a number of chosen locations of a particular component under the influence of a particular unit load. Using the influence coefficient matrix (A), and other information, computer 206 may calculate strain data associated with one or more components of work machine 100, or for the entire machine itself (Step 435.) Details regarding the strain calculations performed by computer 206 are further described below in connection with FIG. 7.

In another embodiment, the load(s) determined by computer 206 in Step 415 may be used to determine a payload of work machine 100 during its operations (Step 440). Details of the payload determination processes performed by computer 206 are further described below in connection with FIG. 10.

In another embodiment, the measured data collected and/or determined by computer 206 in Steps 405 and 410, as well as the strain(s) calculated in Step 435, may be used to determine the fatigue life of one or more components of work machine 100, or of work machine 100 itself (Step 445). This information may also be used to determine damage of the one or more components of work machine 100, or of machine 100 itself. (Step 450).

Also, in another embodiment, the calculations performed by monitoring system 200 may produce result data that may be used to update the information stored in database 208 (Step 460). For example, information reflecting the payload determined in Step 440 may be stored in database 208 for subsequent processing by computer 206 or an off-board system interfaced with work machine 200 via communication network (e.g., wireline or wireless network). Further, any damage data for a particular component(s) determined in Step 460, may be stored as information in database 208 that is also accessible for subsequent analysis and processing. Similarly, the calculated strains and fatigue life information determined in Steps 435 and 445 may be stored in database 208. In this regard, embodiments may continuously update information reflecting the health and use of one or more components of work machine 100, or of work machine 100 itself, thus providing up-to date status information reflecting the operation of work machine 100, and its components.

Additionally, the data collected and calculated by monitoring system 200 may be used to classify an operation of work machine 100 (Step 465.) For example, the measured and determined data produced by Steps 405 and 410, the unknown loads determined in Step 420, the coordinate system transforms determined in Step 425, and the calculated strains obtained in Step 435, may be used by computer 206 to automatically determine a current operation of work machine 100. Details regarding classifying operations of work machine 100 are described below in connection with FIG. 9.

Calculating Unknown Loads to Obtain Free Body Diagram

Figure 5:
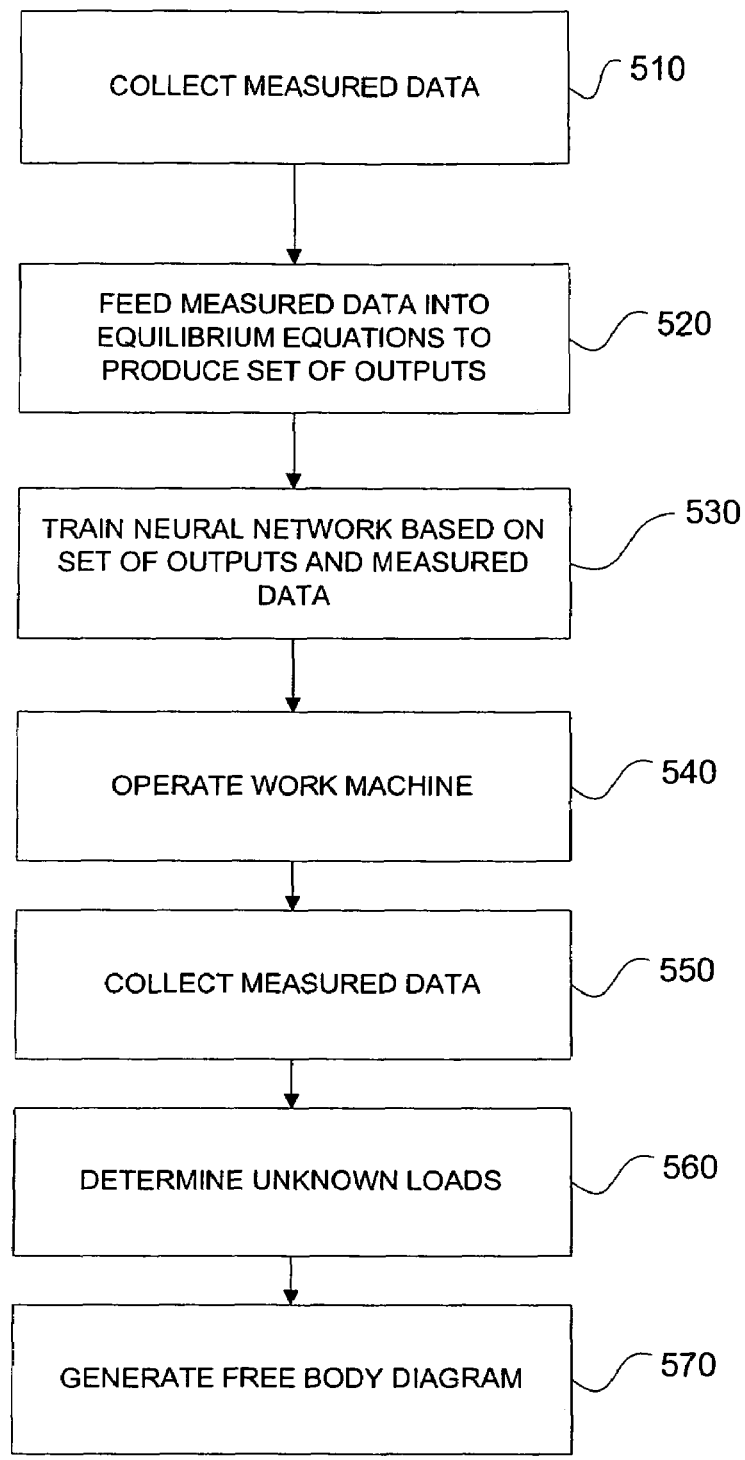
FIG. 5 is a flow chart of an exemplary process for determining unknown loads, consistent with certain disclosed embodiments.

As explained, methods and systems consistent with certain embodiments enable monitoring system 200 to calculate unknown loads associated with one or more components of work machine 100. In one instance, computer 206 may use a neural network to determine unknown loads during operation of work machine 100. In certain embodiments, the unknown loads may be used to generate a free-body diagram of a given component of work machine 100. FIG. 5 illustrates an exemplary unknown load determination process consistent with certain embodiments.

Initially, the neural network used to determine the unknown loads should be trained. To do so, in one embodiment, a testing process may be performed before monitoring system 200 performs run-time determinations of unknown loads. The testing process may be performed for each of a fleet of work machines, for each type of work machine, etc. that is installed with monitoring system 200. For exemplary purposes, work machine 100 is described as being exposed to the testing process, although it should be noted that a work machine of a similar type of machine 100 may be used in lieu of testing work machine 100 to train the neural network.

During testing, work machine 100 is operated for a predetermined time, under one or more operational conditions. During this time, measured data is collected (Step 510). The measured data may correspond to a specific set of measured data, and collected via sensors that measure forces, and sensors that measure strains representing forces experienced by one or more, or all, components of work machine 100. The measured data may then be used as values in, for example, Newtonian static equilibrium equations, that generate output values reflecting unknown loads of specified locations of one or more components of work machine 100 (Step 520). These output values, along with the specified set of measured data, are fed into a neural network to train the network to provide predicted unknown loads within a predetermined threshold (e.g., unknown load values within a certain percentage value of the unknown load values calculated using the Newtonian static equilibrium equations) (Step 530). If the neural network does not produce results within the predetermined threshold, the weights associated with the network may be adjusted until the network produces unknown load output values that meets the predetermined threshold criteria.

In one embodiment, the weight values of the network may be defined based on information determined during previous training of the neural network. In one embodiment, the neural network may be trained based on calculated load values associated with areas of a machine component that are not monitored by sensors during real time operations. These calculations may be performed using a mechanism analysis software package, such as Pro-Mechanica Motion, that simulates the operation of work machine 100 using test data as input. The unknown loads would be calculated as output, and would be used to construct the neural network training set.

Once the neural network is trained, its may be stored in a memory device that is accessible by computer 206 for execution during operation of monitoring system 200. Subsequently, work machine 100 may perform operations (Step 540). During these operations, computer 206 collects measured data in a manner similar to the processes described above in connection with Steps 405 and 410 of FIG. 4 (Step 550). The measured data (e.g., measured force data and strain data reflecting forces on given components) are fed into the neural network, which produces output values reflecting estimates of the unknown loads of work machine 100 (Step 560).

Figure 6:
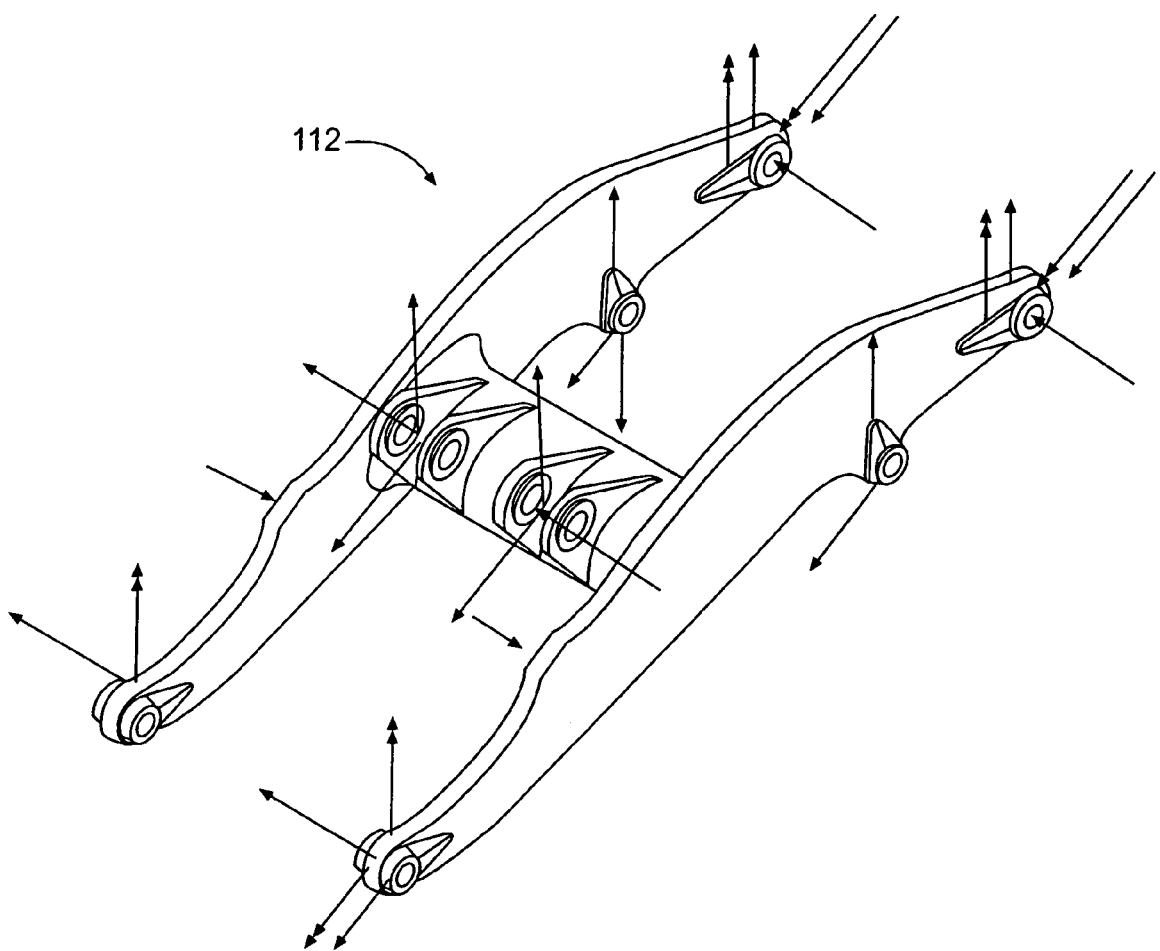
FIG. 6 is a diagrammatic illustration of an exemplary lift arm consistent with certain disclosed embodiments.

In one embodiment, once computer 206 determines the unknown loads, it may also execute software that associates all of the determined load data to the coordinate systems corresponding to one or more respective components of work machine 100. This process allows computer 206 to generate a free-body diagram of one or more, or all of the respective components of work machine 100 (Step 570). FIG. 6 shows one example of lift arm 112 with its associated loads (shown as arrows without their respective load data values) in a free body form illustration. As shown, lift arm 112 may include twenty-eight externally applied loads. Only some of these loads may have been directly measured by one or more sensors 210-228. The remainder of the loads may be calculated based upon the known loads in the manner described above in connection with Step 420. Computer 206 may resolve the load data into the appropriate coordinate system for any structural component using known algorithms, such as trigonometric calculations, that may vary for each type of work machine 100 and/or each type of component of work machine 100. Alternatively, computer 206 may execute neural network software that has been trained to estimate loads in the correct coordinate system of a particular component, such as lift arm 112. It should be noted that FIG. 6 shows an illustration of one component of work machine 100 including coordinate-based loads. The determined load data, relative to their respective coordinate data, is stored as data in a memory location that may be used to perform other processes consistent with certain disclosed embodiments.

Calculating Strain and Determining Fatigue Life

Figure 7:
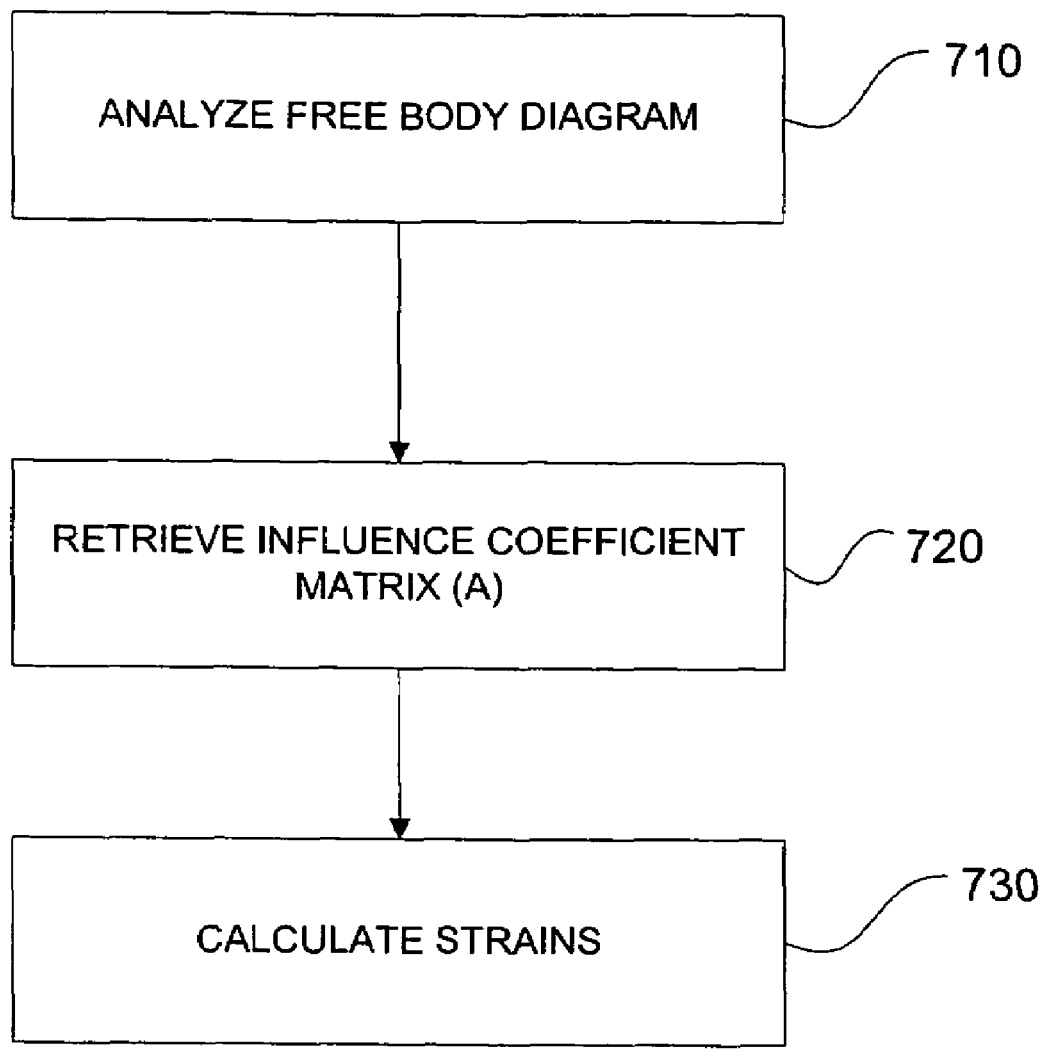
FIG. 7 is a flowchart of an exemplary strain calculation process consistent with certain disclosed embodiments.

As explained, computer 206 may execute software that calculates strains acting on one or more components of work machine 100. FIG. 7 shows a flowchart of an exemplary strain calculation process consistent with certain disclosed embodiments. Initially, computer 206 may retrieve and analyze the free body diagram(s) previously determined by computer 206, and described above in connection with FIGS. 5 and 6 (Step 710). Depending on the strains being determined, computer 206 may retrieve and analyze one or more free body diagrams. For example, to determine all strains acting upon work machine 100, computer 206 may retrieve and analyze the free body diagram data associated with all components of work machine 100. Alternatively, if computer 206 is determining the strain of a particular component, it would retrieve and analyze the free body diagram associated with that component. In certain embodiments, when determining the strains acting on work machine 100, computer 206 may process free body diagrams one at a time, to later analyze the calculated strains of each respective component.

As noted above in connection with FIG. 4, computer 206 may execute software to calculate the strains using an influence coefficient matrix (A). As such, computer 206 may retrieve and populate matrix (A) corresponding to the respective component(s) associated with the strains being calculated (Step 720). Each column of matrix (A) may represent the strain response at a number of chosen locations of a particular machine component (e.g., lift arm 112 shown in FIG. 6) under the influence of a particular unit load, with all other loads set to zero.

In one embodiment, the influence coefficient matrix (A) may be determined by known unit load analysis of a finite element model of the given component, as is known in the art. In another exemplary embodiment, instead of analysis of a finite element model, computer 206 may experimentally determine data for selected rows of the influence coefficient matrix (A) for the given machine component during selected time periods of operation of work machine 100, such as initial operation time periods ranging from start-up of the machine to a certain time period thereafter (e.g., one or more minutes, hours, etc. later). During these time periods of operation, the given component for the matrix under construction may be presumed to be structurally sound (e.g., having no fatigue flaws or cracks). Thus, while the component is deemed structurally sound, the influence coefficient matrix (A) may be determined by measuring strains on the component, and performing a least squares fit between the known external loads on the component and the measured strains. Based upon the results of the least squares fit calculation, the influence coefficient matrix (A) may-be populated with the correct entries. Thus, experimentally determining rows in the influence coefficient matrix (A) may be used for high-stress gradient areas in the given component that may be difficult to model using the finite element method.

The fundamental relationship between measured strain and applied load for a quasi-static body is given by the equation below.

$$\underset{(r\times 1)}{s} = \underset{(r\times n)}{A} \underset{(n\times 1)}{f}$$

where r=no. of measured strain channels on a body, and n=no. of external loads on a body. The influence coefficient matrix (A) may be populated row-by-row. In one embodiment, the first row of the above equation may be written in a time-dependent column vector form, for k time steps into the future, as shown below.

$$\begin{Bmatrix} s_1(t_0) \\ s_1(t_0 + \Delta t) \\ s_1(t_0 + 2\Delta t) \\ \vdots \\ s_1(t_0 + k\Delta t) \end{Bmatrix} = \begin{bmatrix} f^T(t_0) \\ f^T(t_0 + \Delta t) \\ f^T(t_0 + 2\Delta t) \\ \vdots \\ f^T(t_0 + k\Delta t) \end{bmatrix} \begin{Bmatrix} a_{11} \\ a_{12} \\ a_{13} \\ \vdots \\ a_{1n} \end{Bmatrix}$$

The least-squares best-fit solution for the unknown elements in the first row of the influence coefficient matrix is given by the following equation.

$$a_1' = [F^T F]^{-1} F^T s_1$$

The above calculations may be repeated for the remaining rows of the influence coefficient matrix (A). In one embodiment, the number of iterations (i.e., k) that may be necessary for computer 206 to generate an influence coefficient matrix (A) that is satisfactory for all time periods of operation may be dependent on the amount of load data to be obtained. For example, the number of iterations k may continue until test data for each of the different loads has been obtained.

Once the influence coefficient matrix (A) has been fully populated, computer 206 calculates the strain using, for example, known matrix multiplication techniques (Step 730). For example, computer 206 may calculate the strain by multiplying a column vector including data reflecting the external loads experienced by the given component by the influence coefficient matrix (A). The results of the matrix multiplication representing the calculated strain for the given component may be stored in a memory location for subsequent processing. In one embodiment, computer 206 calculates the strain for each of the monitored components of work machine 100 to provide a representation of the strains experienced by machine 100 during operation.

In accordance with certain embodiments, computer 206 may also execute software that performs fatigue life calculation processes to estimate the life of a given machine component and/or work machine 100. The fatigue life calculation process may accept strain values that are calculated from the multiplication of the external loads on the component by the influence coefficient matrix as input, or directly measured strain values may serve as input. In this manner, an additional measure of system robustness can be attributed to monitoring system 200.

In certain embodiments, fatigue life calculations may be performed based on the measured data collected and determined in Steps 405 and 410 of FIG. 4. Additionally, as noted above, fatigue life calculations may be performed using the calculated strains determined in Step 435 of FIG. 4, and further described in FIG. 7.

Computer 206 may execute a software process that performs fatigue life algorithms that estimates the life of one or more components of work machine 100. Computer 206 may calculate the fatigue life of components having associated with them one or more strain gauges, such as strain gauges configured in the form of a wireless node 228. This measured strain data, or the strain data calculated in Steps 435 of FIG. 4, may be used to estimate the accumulated damage in these areas. In one embodiment, estimated fatigue damage may be determined using rainflow analysis followed by an application of Miner's rule. Rainflow analysis is a method to count the cycles in complex, random loading of components. Miner's rule may then be used to sum the resulting damage at each point of interest of a component. This information, may provide an assessment of the structure of work machine 100. The fatigue damage estimated by Miner's rule effectively provides an estimate of remaining structural life.

For example, to determine the fatigue life of a component, a stress-life curve may be used for the welded joints, while a stress-life curve with Goodman mean stress correction may be used for other remaining structures associated with a component. In addition, separate strain-life curves may be used as desired for certain locations, such as a strain-life curve with Morrow mean stress calculation. As known in the art, computer 206 may execute software that performs the following equation may to determine fatigue life based on applied stresses.

$$\log N = \log a + d \cdot \log \sigma - m \cdot \log S$$

N: number of cycles
a: life intercept; constant for each curve
d: d=0 for B50 curve, d=−1.28 for B10 curve
σ: standard deviation; constant for each curve
m: slope of the curve; constant for each curve
S: stress range=2*Sa (Data)

A Goodman mean stress correction may be conducted using the equation shown below.

$$\frac{S_a}{S_{a0}} + \frac{S_m}{S_u} = 1$$

$S_a$: stress amplitude with $S_m$ (Data)
$S_{a0}$: modified stress amplitude for 0 mean stress
$S_m$: mean stress (Data)
$S_u$: ultimate strength=material constant The fatigue damage estimated by Miner's rule effectively provides an estimate of remaining structural life. Fatigue life calculations utilizing a strain-life approach may be carried out using one of the equations below.

$$\varepsilon_a = \frac{\Delta \varepsilon}{2} = (\sigma'_f / E) \cdot (2N)^b + \varepsilon_f \cdot (2N)^c$$

$\epsilon_a$: strain amplitude (Data)
$\Delta \epsilon$: strain range (Data)
N: number of cycles
$\sigma_f'$: fatigue strength coefficient; material constant
E: Young's modulus; material constant
b: fatigue strength exponent; material constant (negative value)
$\epsilon_f'$: fatigue ductility coefficient; material constant
c: fatigue ductility exponent; material constant (negative value)

Morrow mean stress ($S_m$) correction may be incorporated as in the equation below.

$$\varepsilon_a = \frac{\Delta \varepsilon}{2} = ((\sigma'_f - S_m)/E) \cdot (2N)^b + \varepsilon'_f \cdot (2N)^c$$

The fatigue life may also be calculated from strain obtained by using the influence coefficient matrix (A) and the external loads as described above. In such embodiments, flags associated with the rows of the influence coefficient matrix (A) associated with the location of interest of a component may be activated by a user or software process executed by computer 206. For example, if an unexpected fatigue problem develops at some location that is not equipped with a strain gage, the rows of the influence coefficient matrix (A) associated with that location could be activated by altering the value of a flag associated with those rows.

The results of the fatigue life calculations may reflect estimated fatigue life for one or more components of machine 100, as well as an estimate for the fatigue life of the entire structure of machine 100, or portions thereof. Computer 206 may store the fatigue life calculation results in a memory, such as vehicle database 208, for subsequent access and analysis.

As the work machine 100 continues to perform operations, the present age of the machine (designated below as $t_{now}$) may creep into the probability density function associated with the distribution of fatigue life, $f(t)$. In one embodiment, computer 206 executes software processes to determine an altered fatigue life distribution for that component based on Bayes theorem. For example, the probability that the fatigue life will be less than some arbitrary time in the future, t*, is given by the following equation.

$$p(\text{life} < t^*) = \frac{\int_{now}^{t^*} f(t)dt}{\int_{now}^{\infty} f(t)dt}$$

The updated probability density function may then be calculated as in the following equation.

$$f_{up}(t^*) = \frac{dp(\text{life} < t^*)}{dt^*}$$

The new expected life (i.e. the mean value of the updated probability density function) is given by the following equation.

$$t_{up\_mean} = \frac{\int_{now}^{\infty} t^* f_{up}(t^*) dt^*}{\int_{now}^{\infty} f_{up}(t^*) dt^*}$$

Applying the Bayesian approach by computer 206, may avoid user confusion that may result when the machine hours exceed an original estimated time for crack initiation with no visible crack present at the component location under analysis. The results of the Bayesian calculation process are also stored in a memory device, such as database 208, for subsequent access and use by other processes consistent with the disclosed embodiments.

Damage Detection

In certain embodiments, computer 206 may also be configured to execute software that performs a damage detection process for work machine 100. The damage detection process may include performing a linear regression analysis between the calculated strains determined at step 435 of FIG. 4 and the measured strain data obtained at step 410. For example, computer 206 may perform software processes that generates a function reflecting the linear regression analysis of the strains calculated in step 435 of FIG. 4 and the measured strain data determined in step 410 of FIG. 4. The function may be generated based on a graph bounded on the X-axis by the calculated strains and on the Y-axis by the measured strains. By analyzing the slope and/or correlation coefficient of the of the linear regression analysis within this graph, computer 206 may determine whether damage exists in the component associated with the strains under analysis. For example, if the slope of the function generated by the regression analysis is not within a certain threshold of "1," computer 206 may determine damage exists in the component. The damage detected may be a fatigue crack, a loose bolted joint or other type of failing joint, and any other form of structural failure associated with a component of work machine 100.

This embodiment may be further explained based on the influence coefficient matrix used to calculate strains. In certain embodiments, the influence coefficient matrix (A) is populated early in the work machine's life. Thus, strains calculated during this time frame using matrix (A) may be not be different from the actual measured values. Later in work machine 100's life, the strain values measured and determined by monitoring system 200 may change values. Thus, when calculating strains at this stage of work machine 100's life, matrix (A) does not accurately reflect the strain response of work machine 100 at that time. Therefore, comparing the calculated strains with the measured strains using the linear regression analysis may result in a function having a slope different from "1," reflecting the difference in strain values between the calculated and measured strains. This difference may reflect a crack, bend, or similar damage to an analyzed component. Computer 206 may use rules or other forms of intelligence to determine the level of damage based on the difference of the resulting function's slope to the target value of slope "1." For example, the amount of detected damage may be proportional to the difference in the function's slope from "1." That is, larger differences between the function's slope from the target value may represent more damage in the analyzed component.

The results of the damage detection process may be stored in a memory device, such as database 208, for subsequent access and use by processes consistent with the disclosed embodiments. In certain embodiments, computer 206 may report the damage to the operator of work machine 100 via a display device or similar warning indicator. Further, computer 206 may generate a damage report and store the information in database 208. An off-board system, such as a laptop, server computer, another work machine's computer, etc., may access database 208 via a communication network interconnecting the off-board system and work machine 100, such as a wireline or wireless network. Alternatively, computer 206 may receive a request from an off-board system to send damage reports. In response to the request, computer 206 may retrieve the damage report stored in database 208 and send the report to the requesting off-board system. In another embodiment, computer 206 may perform the damage detection process in response to the request from the off-board system. Alternatively, computer 206 may perform software processes that automatically direct computer 206 at periodic times to perform the damage detection process and report the results of the process to predetermine target systems, such as a particular off-board system. It should be noted that the damage detection results may be accessed and processed by any type of on-board or off-board system, and the above examples are not intended to be limiting to the disclosed embodiments.

Operation Classification

As explained, methods and systems consistent with certain embodiments may determine the operation being performed by work machine 100 based on different types of information. For instance, in certain embodiments, computer 206 may execute software that classifies a current operation being performed by work machine 100. Classification of the current operation may include an analysis of the loads acting on work machine 100, as well as any other sensed or derived parameters, including, for example, inclination relative to the earth, ground speed velocity and/or acceleration, positions, velocities, and accelerations of the implement, and/or pressures. One method of classifying the operation would be to use traditional deterministic software programming techniques. Alternatively, these parameters may be fed into a neural network for analysis to classify the current operation. In one example, the neural network may classify the current operation into one of the following operations: (1) roading with no load; (2) digging; (3) roading with a load; (4) dumping; (5) idling; (6) bulldozing; (7) back-dragging; and (8) other. Other classifiable operations may be used. Further, while the exemplary operations may be appropriate when work machine 100 is a wheel loader, they may not be appropriate for a different type of work machine, such as, for example, a motor grader or hauling machine. Thus, computer 206 may execute software that classifies operations that are specific to the type of work machine 100, which may include the same or different types of classified operations for other types of work machines.

Figure 8:
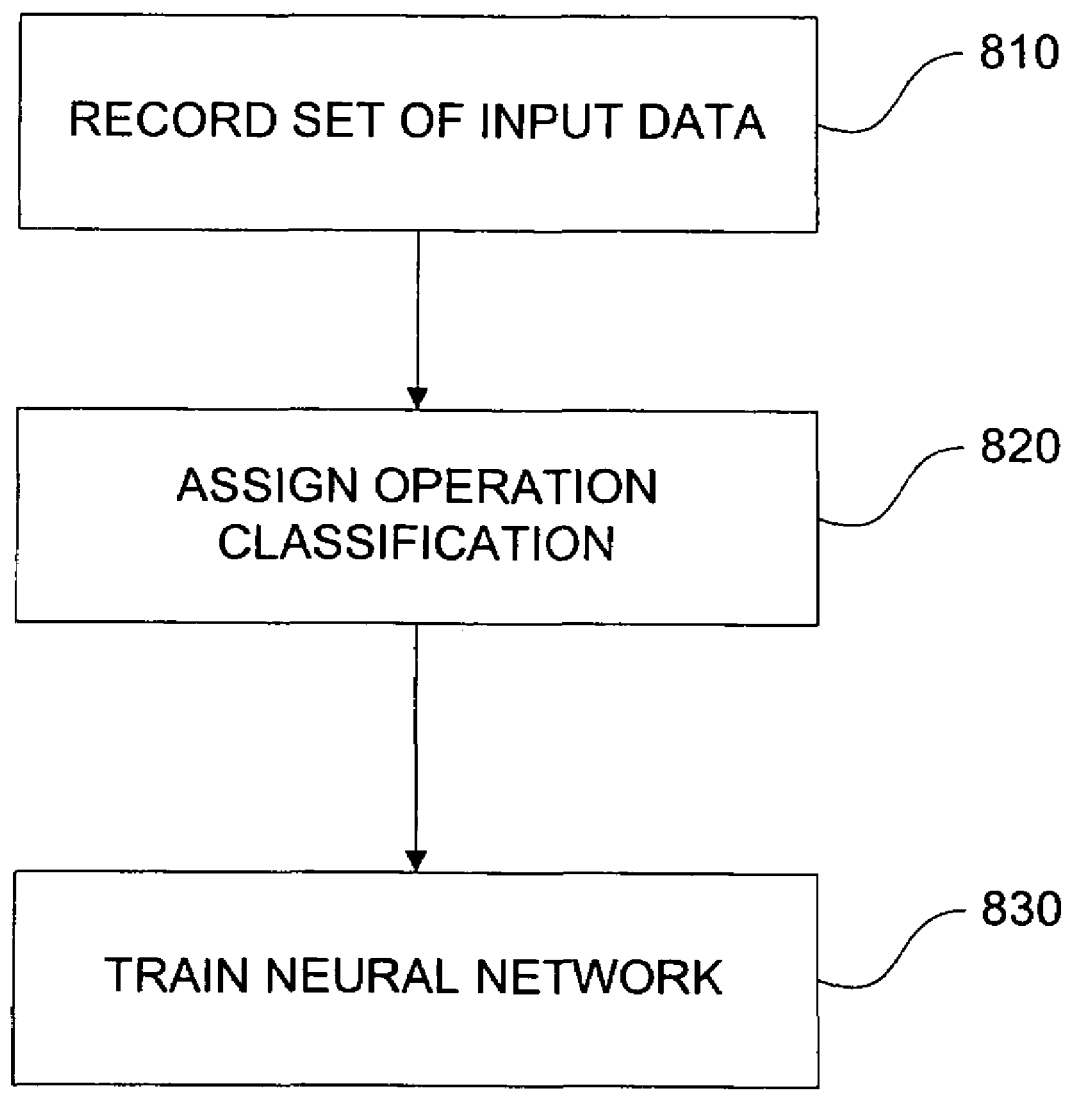
FIG. 8 is a flowchart of an exemplary neural network configuration process consistent with certain disclosed embodiments.

In embodiments implementing a neural network for operation classification, database 208 may be installed with a neural network that is configured to produce output values reflecting certain operations associated with the type of work machine 100. FIG. 8 shows a flowchart of an exemplary neural network configuration process consistent with certain disclosed embodiments. To configure the neural network to perform operation classification functions, actual operational data associated with the operation classifications are first recorded in a memory device during operation of work machine 100 (Step 810). For instance, sensor data may be collected by computer 206, or another device configured to collect operational data from work machine 100. The recorded data may also include time stamp information that reflects when particular data values for each sensor data is obtained during machine operations. The recorded sensor data values (e.g., data values reflecting the measured parameter, such as strain, ground speed velocity, etc.) are designated as inputs, which are assigned to time periods associated with the operation of work machine 100 during data collection. Thus, each data input may include a set of data inputs arranged as a function of time (e.g., input $1(t1)$, input $2(t2), \ldots ,$ input I(tI), where I may be any positive integer). Based on this information, a user or computer-executed process may assign an operation classification to each of the time periods associated with the input data (Step 820). For example, minimal forces or strains may be applied to certain components of work machine during idle time periods. Accordingly, the user or software process may assign an idle operation classification to the time periods having data input values reflecting these minimal forces or strains.

Once operation classes are assigned to the data inputs for the measured time periods, the classified data inputs are fed into a neural network as inputs in order to train the network to accurately classify operations during real time operation of work machine 100 (Step 830). For instance, in one embodiment, the data inputs are applied to the neural network to produce, as output data, a predicted set of classified operations for each time period (e.g., time periods 1-I). Further, work machine 100 may be exposed to real operations associated with each of the classified operations. During these operations, computer 206, or another internal or external machine device, may collect actual sensor data. Computer 206, or a testing system, may then compare the predicted output classification data values with the actual classification of the operations performed during the real time operations of work machine 100 to determine whether the neural network predicts the operations of machine 100 during each of the time periods within a predetermined criteria. The predetermined criteria may be associated with a threshold value that reflects a maximum acceptable difference between the actual and predicted classification output values. One skilled in the art would recognize that a number of different conditions, thresholds, etc. may be applied as the predetermined criteria by the disclosed embodiments. If the neural network does not meet the predetermined criteria, the network may be adjusted and re-tested until the predetermined criteria is met. Once the neural network produces accurate predicted classifications, the network may be stored in database 208 for subsequent use in classifying operations of work machine 100 during later real time operations.

In another embodiment, a process may be implemented that allows a user to classify operations of a work machine under test conditions. In this exemplary embodiment, a work machine (e.g., work machine 100) may perform one or more operations over a predetermined period of time. During operation, sensors on the work machine collects measured data associated with one or more components of the machine. Further, the operation of the work machine may be videotaped or monitored in some form. Subsequently, a user may view a time stamped video clip of the work machine during the recorded operations and assign operations to certain time periods of the operation. This time stamped operation data and the collected measured data is correlated as classification data as a function of time. The classification data may be fed as the inputs into the neural network for training the network in a manner similar to that described above (e.g., train the network until the predetermined threshold criteria is met).

In one embodiment of the present invention, when the neural network does not meet the predetermined criteria, a user or computer executed process, such as program code executed by computer 206, may adjust the weights associated with links corresponding to the nodes within the neural network to compensate for previous inaccurate predictions of operation classification output values. For example, if the neural network includes more than one level of nodes, the weights associated with each link interconnecting the layered nodes may be adjusted to train the network to produce more accurate output values. The weight adjustments may be performed by any number of known algorithms used for training neural networks, such as algorithms associated with radial basis function approximations. One skilled in the art would recognize that certain embodiments of the present invention may employ different algorithms that affect the learning process of the neural network.

Although the above exemplary embodiment describes the neural network being stored in database 208, the network may also be trained after it is stored in a memory device located in machine 100. Further, the neural network (trained or untrained) may be stored in a memory device internal to computer 206 or any other electronic component within work machine 100. As such, embodiments are not limited to the above examples.

Figure 9:
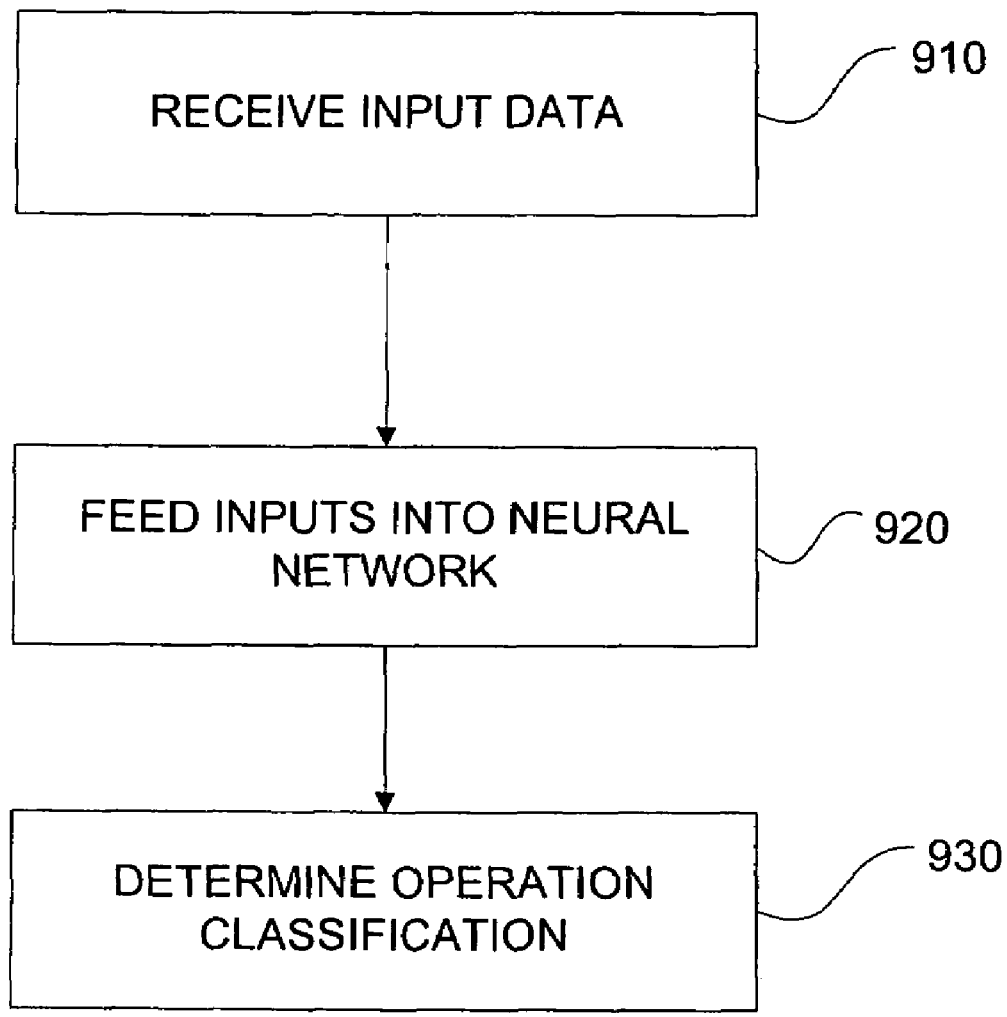
FIG. 9 is a flow chart of an exemplary operation classification process consistent with certain disclosed embodiments.

Once the neural network is trained and provided in work machine 100, computer 206 may perform an operation classification process that determines the type of operation performed by work machine 100 during certain time periods of operation. FIG. 9 is a flowchart of an exemplary operation classification process consistent with certain disclosed embodiments. In addition to strain data, computer 206, or another component of work machine 100, may receive sensor data as inputs from sensors 210-228 (Step 910). The received sensor data may reflect operational parameters associated with operations of work machine 100 over a period of time. According, the received parameter data may be time stamped by sensor 210-228 or computer 206. The received parameter data may be checked for reliability, in a manner similar to the processes described below in connection with steps 420 of FIG. 4.

The received data may then be fed as inputs into the trained neural network stored in database 208 (or elsewhere) (Step 920). Additionally, computer 206 may feed other information as inputs to the neural network. For example, unknown load data, free body diagram data, and calculated strain data may be used as inputs to the network. The neural network processes the inputs using known neural network processes and produces output values. Based on the output values, computer 206 may determine the classification of an operation performed during certain periods of time of operation of work machine 100 (Step 930). For instance, based on parameter data values associated with one or more work machine components, computer 206 may determine at time ti, work machine 100 was roading with no load, digging, roading with a load, dumping a load, etc. The operation classification information may be stored in a memory location within a memory device (e.g., database 208, local memory within computer 206, etc.) for subsequent processing consistent with certain disclosed embodiments.

It should be noted that computer 206 may execute more than one neural network to perform any of the neural network processes-described above. For example, one neural network may be used to classify the current operation, while a second neural network may be used to determine the unknown loads of a machine component.

Payload Determination

As described, methods and systems consistent with certain embodiments enable computer 206 to execute software that estimates the payload carried by work machine 100 based on the measured data. Some payload determination systems may require that the operator pause the work machine and then request an estimate from the system just before dumping the load. Pausing the work machine ensured that inertial forces would not corrupt the payload determination. The disclosed embodiments enable payload determinations to take place without pausing the work machine during dump operations.

Figure 10:
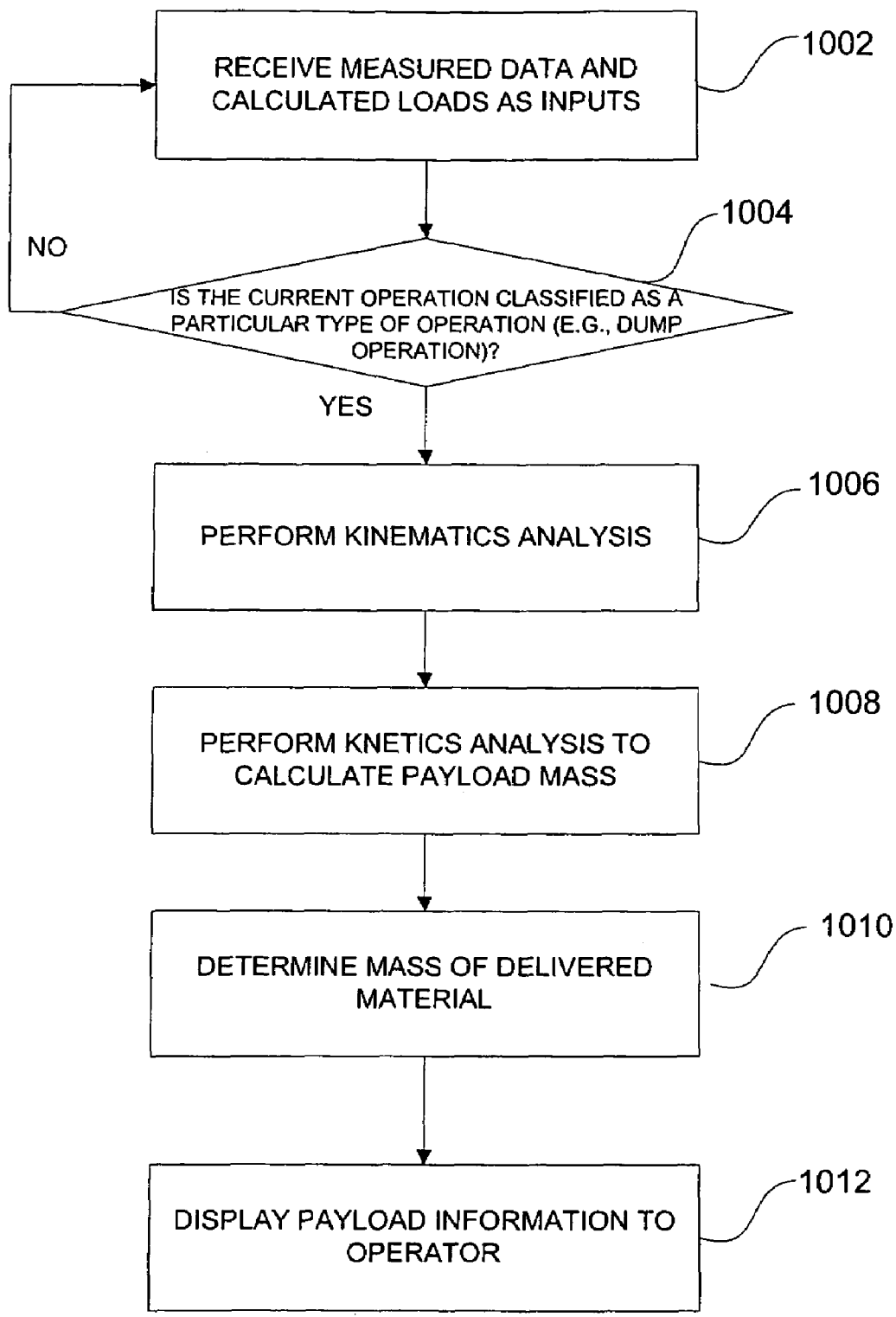
FIG. 10 is a flow chart of an exemplary payload determination process consistent with certain disclosed embodiments.

FIG. 10 shows a flowchart of an exemplary payload determination process 1000 consistent with certain embodiments. At a step 1004, based on the results of the operation classification process described above in connection with FIG. 9, computer 206 determines whether the current operation is classified as a certain type of operation, such as a dump operation. If the current operation is not classified as a dump operation (Step 1004; No), then the payload determination process returns to step 1002. The payload determination process continues to loop until the current operation is classified as a dump operation. It should be noted that the dump operation is an exemplary operation used by computer 206 during the payload determination process. The disclosed embodiments contemplate using other types of classified operations to determine whether to calculate the payload of work machine 100.

When the current operation is classified as a dump operation (Step 1004; Yes), computer 206 may perform a kinematics analysis to determine and consider the motion of work machine 100 and/or one or more of its components, such as work implement 118 (Step 1006). Further, computer 206 may perform a kinetics analysis to calculate and determine the payload mass (Step 1008). The kinetics analysis may include determining the mass M from a derived expression for the payload, M=f($q_i$). In the expression for the payload, time derivatives of measured quantities q appear. These may be calculated via numerical differentiation using a three-point central difference method, shown in the equation below.

$$\frac{dq}{dt}(t_n) \approx \frac{q_{n+1} - q_{n-1}}{2\Delta t}$$

In the equation, $\Delta t$ is the time increment between each sampled value. Determining the mass of the load may be performed by solving -for the necessary unmeasured variables, such as, for example, loads at non-instrumented pins and other unknowns. In one exemplary embodiment, computer 206 may execute software that solves, for example, a 10×10 system for ten variables that contribute to determining the payload of work machine I 00. In one exemplary embodiment, the 10×10 system may be combined into a single, derived analytical expression to determine the payload using methods known in the art. The derived expression for the payload, M=f($q_i$) may account for all inertial effects during the loading and dumping process. The expression M=f($q_i$) is derived from a set of Newtonian equations of motion for the front linkage of work machine 100. Algebraic manipulations are performed to reduce all of the equations to a form M=f($q_i$). The Newtonian equations of motion involve variables related to inertial effects so that these effects can be accounted for in the payload calculation. Accordingly, an operator may no longer need to pause work machine 100 to allow the machine to calculate its payload. Further, computer 206 may be configured with software that, based on the operation classification of work machine 100, automatically determines payload at predetermined times, such as when work machine is about to perform a dump operation, during roading with load, etc.

In one exemplary embodiment, computer 206 may execute software that determines different stages of a dump operation once this operation is classified. For instance, computer 206 may execute software that determines different stages of a dump operation based on the positions and load data of one or more components of machine 1 00 during a classified dump operation. Accordingly, computer 206 may detect when work machine is beginning, performing, and ending a dump operation. Based on this knowledge, computer 206 may perform the above described kinematics and kinetic analysis processes at both the beginning and end of the determined dump operation. In this regard, computer 206 may determine the mass of the delivered material by determining the difference between the mass of the payload at the beginning of the dump operation and at the end of the dumping operation (Step 1010). Therefore, the payload calculation may reflect the mass of delivered material, even when only a part of the payload is dumped.

In one exemplary embodiment, the determined payload may be optionally displayed in an operator interface located in the operators' station 110 (Step 1012). This may allow an operator to track the weight of material being dumped by work machine 100. In addition to the payload amount, the display may convey additional information to the operator, including, for example, an impending tip-over alert and a maximum load scenario, both of which may be determined by computer 206 based on determined load and strain data, as well other measured parameters, such as inclination relative to the Earth. The display could be in the form of an audible noise, lights, and a liquid-crystal display, among others.

Computer 206 may store data reflecting the calculated payload in a memory device, such as vehicle database 208. To this end, computer 206 may perform a process that determines a cumulative payload for a given time period based on previously calculated and stored payload information. The cumulative payload information may be maintained in database 208, and displayed in a display device in operator's station 10, and downloaded off-board work machine 100 for subsequent processing.

In another embodiment, computer 206 may execute neural network software that is trained to determine payload of machine 100 based on measured stress data, determined load data, and other collected parameter information. In another embodiment, monitoring system 200 may interface with some other pre-existing payload determination system rather than rely on the processes for payload determination described here.

INDUSTRIAL APPLICABILITY

Methods and systems consistent with the disclosed embodiments use collected sensor data and calculated strains, loads, and operational information, to provide estimates of fatigue life, payload, and damage state of one or more components of a work machine. This information is used to provide insight on the fatigue life and health of the work machine, and to gather information useful for future design improvements of work machines. In certain embodiments, the information determined by health and usage monitoring system 200 may be useful to design future work machines, operate work machines, to determine resale values based on known wear of work machine 100, and/or when to perform maintenance and repair. For example, the health information obtained be the disclosed embodiments may be used to design components of a work machine that account for wear that has been analyzed from real time operation of similar machines. In addition, health and usage monitoring system 200 may provide health information that is relevant and useful to a number of entities, including machine operators, work machine purchasers, service mechanics, and work machine developers and engineers. Such relevant information may include, 1) cumulative damage data, 2) machine operation distribution, 3) extreme load cases for each component, 4) load histories at various severity levels, 5) damage rate histogram, and 6) crack detection. Each of these items is described further below in turn.

Information regarding cumulative damage data may be stored within vehicle database 208 and may be made accessible to one or more users or computer 206. In certain embodiments, health and usage monitoring system 200 may continuously update the stored data that is representative of the structural health and usage of the monitored component of work machine 100. Users or computer processes may access the cumulative fatigue data to estimate the residual life and/or value of a particular component, set of components, or work machine. Such information is relevant to those purchasing and/or selling work machines that have been previously operated.

In one exemplary embodiment, instead of continuously storing damage related data for all locations of each of the monitored components, health and usage monitoring system 200 may track accumulated damage only at discrete locations, such as at the locations where one or more sensors are actively sending signals to computer 206. Further, health and usage monitoring system 200 may optionally accumulate damage data via the calculated strain at a number of desired component locations, as determined by a user. In one exemplary embodiment, the cumulative damage may be partitioned into portions attributable to each of the various work machine operations. For example, in a wheel loader work machine, health monitoring system may store cumulative damage data in matrix form. Each row of the matrix may correspond to a particular location of a wireless node 228 and a data value associated with an amount of damage. The matrix may be configured in any form, such as a designated set of columns storing accumulated damage data for each of the classified operations for that work machine. A related column may also store the total damage data for a particular wireless node 228. The damage data may include directional information corresponding to the most likely-orientation of a fatigue crack.

Information regarding the different classifiable operations may be stored within vehicle database 208 and made available to one or more users or computer systems, such as computer 206. The types of operations that may be classified by the disclosed embodiments may vary based on the type of work machine to work machine. For example, a wheel loader may have associated classifiable operations such as, for example, roading with no load, digging, roading with a load, dumping, idling, bulldozing, back dragging, and "other." The classification of these operations may be performed either by a neural network or via deterministic software.

Once classified into a specific operation, computer 206 may execute software that determines the amount of time spent performing an operation in real-time. In one example, computer 206 may store this information in vehicle database 208 as data indicative of a total amount of time that work machine 100 operates in a particular operation. For example, based on collected sensor data, and determined load and other parameter information, computer 206 may determine that work machine 100 is entering a digging operation at a time $t_1$. The operation may continue until computer 206 determines that an operation other than digging is being performed. At that time, computer designates the end of the digging operation at a time $t_2$. The time period between $t_1$ and $t_2$ may be summed with the time periods of other digging operations to maintain a total time period that work machine 100 is operating in a digging operation. Computer 206 may perform software that forms this information in a histogram. Alternatively, computer 206 may download this information to an off-board system that forms the histogram. The histogram also may include information showing a total operation time for each of the other classifiable operations. Alternatively, embodiments may form separate histograms for the other classified operations, or selected combinations of operations. Further, the operation information maintained by health and usage monitoring system 200 may be customized or configured based on desired characteristics. For example, the total time spent working in a classifiable operation need not reflect a total time over the lifetime of work machine 100. Instead, the total time data for the classified operation may reflect the amount of time working in the classifiable operation since a last maintenance job was performed on the machine, the total amount of time working in the classifiable operation at a specific worksite, etc.

Computer 206 also may be configured to execute software that determines in real-time the amount of fatigue of at least one component of work machine 100 over a period of time due to a specific operation. Again, referring to the digging operation as an example, when determining the fatigue, computer 206 may determine that the work machine is entering a digging operation at time $t_1$. The operation may continue until computer 206 determines that the digging operation has ended at time $t_2$. Using any fatigue life calculation processes described above, computer 206 may determine the component's fatigue life by calculating the amount of fatigue that occurred during the time period between $t_1$ to $t_2$. Summing the determined fatigue with the total lifetime fatigue that occurred while performing the operation may provide a total amount of fatigue due to the classifiable operation. Further, the total amount of fatigue may be reflective of fatigue during the work machine's entire operational lifetime, since the machine's last maintenance, since initiating work at a specific worksite, etc. This information may be displayed in a histogram showing the fatigue for each operation separately, collectively, or for sets of selected operations.

In another embodiment, health and usage monitoring system 200 may store information regarding the extreme (e.g., maximum or minimum) instantaneous load scenarios over a machine's or component's lifetime. For example, referring to FIG. 11, a body 1100 is shown under the influence of any number of external loads $f_i$ (i=1 to n). The body 1100 may be a portion of any of the structures comprising work machine 100. When any one of the external loads $f_i$ complies with a pre-established factor, such as surpassing a previously stored lifetime maximum or minimum load value, then computer 206 may update vehicle database 208 with the new lifetime maximum or minimum value. By storing both the lifetime maximum load and the lifetime minimum load, a total range of loading is captured and available for analysis and display on a display device in any format.

In one exemplary embodiment, health and usage monitoring system 200 may store a snapshot of all load values acting on body 1100 at a particular point in time. For example, when any one load value exceeds a pre-established factor of a lifetime maximum or minimum value, computer 206 stores data regarding all the applied load values for body 1100. In one exemplary embodiment, each of the external loads $f_i$ may be considered an element in a column vector f(t). To save the data regarding all the applied loads, the complete column vector f(t) may be saved. It should be noted that each body and each load being monitored by health and usage monitoring system 200 may have its own "extreme load case matrix." The extreme instantaneous load scenario provides information regarding the most devastating instantaneous load applied to the body 1100 for each applied load.

In addition, health and usage monitoring system 200 may associate the lifetime maximum and minimum load values with the work machine's current operation classification in memory. The load data and corresponding operation classification information may be used in designing and developing components for avoiding yield or buckling failures. Thus, in certain embodiments, computer 206, or another machine system, may send the stored load and operation classification information to an off-board computer system for subsequent analysis, such as design, manufacturing, and diagnostic analysis.

In certain embodiments, computer 206 may execute software that stores in database 208 information associated with the load histories at various severity levels for each classified operation over one or more selected time periods (e.g., $t_1$ to $t_2$). This information may be provided to the operator of work machine 100 or to off-board systems for analysis by computer-executed software or a user. For example, the stored information may include data reflecting the loads applied to a given component determined at time $t_1$ (e.g., the beginning of a classified operation) to time $t_2$ (e.g., the end of the classifiable operation) for a desired severity level. A desired severity level may be represented as a percentage value reflecting a level of damage experienced by a given component(s). For example, a 100% severity level may reflect the most damaging example experienced by the component or machine during a given operation. A 50% severity level may represent the average damage experienced by the component or machine during the operation. Accordingly, for example, a user or software process may direct computer 206 to store the load history of the component at the 90th percentile severity level for a digging operation. Computer 206 collects and stores all the loads that occur during the digging operation when the loads amount to a severity level at the 90th percentile. The determination as to whether a particular loading history is at a $90^{th}$ percentile severity level may be made by comparing the damage rate for that particular operation with a known $90^{th}$ percentile damage rate obtained from the damage rate histogram (contained in database 208) associated with some component of work machine 100. In one exemplary embodiment, when a newly collected load history is associated with a severity level that is closer in value to a pre-selected severity level (e.g., a desired level set by a user) than that of a previously saved load history associated with the same severity level, the newly collected load history may be replace the previously stored history in database 208.

Figure 12:
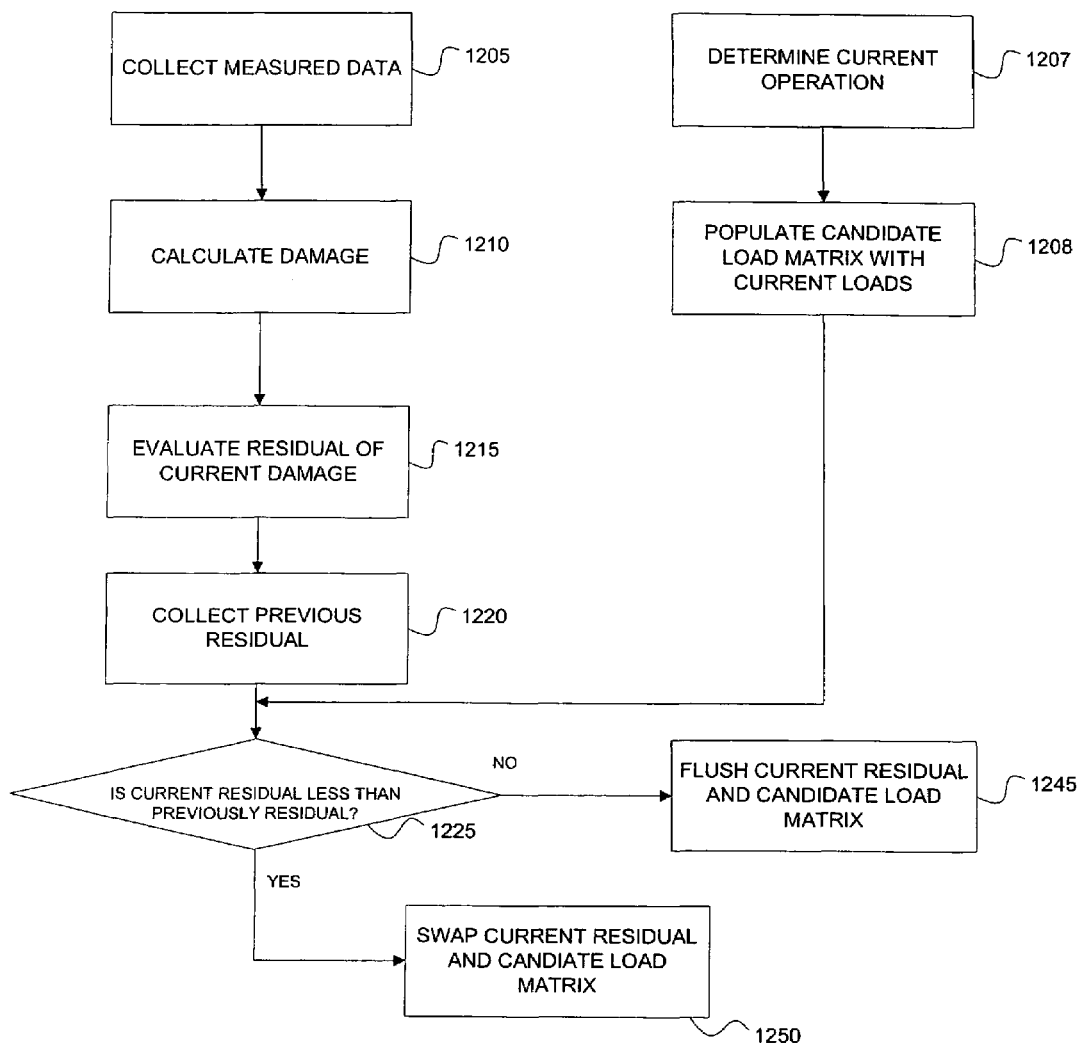
FIG. 12 is a flow chart of an exemplary load history building process consistent with certain disclosed embodiments.

To better illustrate this exemplary embodiment, FIG. 12 shows a flowchart for storing load history information in vehicle database 208. Initially, work machine 100 performs an operation. During the current operation, computer 206 collects measured data and load data in a manner consistent with the process steps described above in connection with FIG. 4 (Step 1205). Computer 206 collects the measured data associated with a given component of work machine 100 at a time $t_1$. Recording may be based on a pre-established first triggering event. In one exemplary embodiment, the triggering event may be associated with the initiation of a classified operation, as determined in a manner consistent with the above disclosed embodiments. For instance, referring to the above mentioned digging operation as an example, computer 206 may detect a first triggering event when it determines work machine 100 has begun a digging operation.

At some point, computer 206 stops recording load data at a pre-established second triggering event at time $t_2$. The second triggering event may be an indication that a classified operation has ended, as determined by computer 206 in a manner consistent with the above disclosed embodiments.

Computer 206 may also determine the current operation performed by work machine 100 during the monitored time period $t_1<t<t_2$ (Step 1207). In one embodiment, computer may execute a neural network to classify the current operation in a manner similar to that described above in connection with FIG. 9. Additionally, computer 206 may collect load data determined by computer 206 in a manner consistent with the disclosed embodiments. The load data may be used to populate a candidate load matrix (Step 1208). The candidate load matrix reflects a data structure including the load history for the component or work machine 100 during the current operation for the given time period t. Thus, the stored load data in the matrix may include all the loads applied to the analyzed component over the time period $t_1<t<t_2$.

Figure 11:
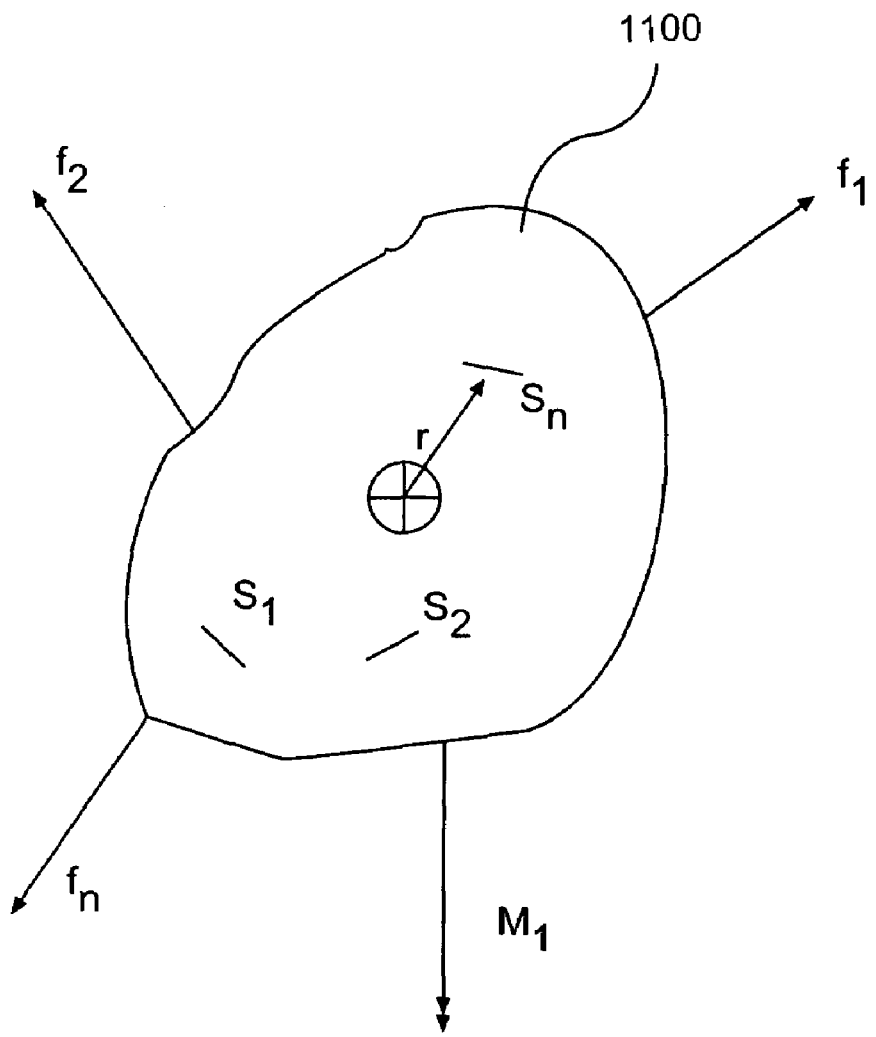
FIG. 11 is a diagrammatic illustration of an exemplary body under load consistent with certain disclosed embodiments.

Computer 206 may also determine a target damage rate for one or more components of work machine 100 for the time period t. The target damage rate corresponds to the desired severity level percentile. Accordingly, if the desired severity level is the 90th percentile for the exemplary digging operation, computer 206 may select the target damage rate to correspond to the 90th percentile damage rate. In certain embodiments, computer 206 may access and analyze a damage rate histogram to determine the target damage rate. For example, the body 1100 of FIG. 11 is shown under the influence of any number of external loads $f_i$ (i=1 to n). The load history for the $i^{th}$ operation, $f_i(t)$ may give rise to a corresponding damage field, $D_i(r,t)$, which is increasing with time. Accordingly, for each of the different operations performable by work machine 100, a complete finite time history (of length $t_2-t_1$) of f(t) may be selected by monitoring the residual of the following equation.

$$\frac{\int_S w(r)D_i(r, t_2)dA - \int_S w(r)D_i(r, t_1)dA}{t_2 - t_1} = \text{target damage rate}$$

As explained above, the target damage rate is the damage rate corresponding to the desired percentile of severity. The damage field, $D_i(r,t)$, is the amount of damage that exists on the component at time t at a particular surface location r (a position vector in the body's local coordinate system) attributable to the $i^{th}$ operation. A weighting function, $w(r)$, is a measure of the relative importance of failure at various locations on the surface of the body being monitored. For example, a weld failure at one location on a body might be more damaging, and more expensive to repair, than a similar failure on another part of the body. The time interval, $t_2-t_1$, for the load history $f_i(t)$ may be equal to the duration of one instance of that operation that most closely satisfies the target damage rate equation. In the target damage rate equation above, the quantities are shown in integral form in order to conveniently convey the concept. In another exemplary embodiment, however, the surface integrals may be approximated in the form of a weighted summation. A total damage field, $D_{total}(r,t)$, may be determined using the following equation.

$$D_{total}(r, t) = \sum_{i=1}^{\text{\# of ops}} D_i(r, t)$$

It should be noted that the direction of damage used for the summation in the above equation must be the same for all of the classifiable operations. Also, it should be noted that an amount of total damage may be different on every plane. Accordingly, the plane having the highest amount of total damage must be the plane utilized when solving for the target damage rate. Again, the location of each wireless node 228 may potentially have a different plane of maximum damage. The target damage rate may be determined prior to or during the current operation of work machine 100.

Computer 206 may also calculate the current damage rate for the component over a time period t of the single digging operation, where $t_1<t<t_2$ (Step 1210). Computer 206 may determine the total damage using the equations for determining the target damage rate described above, based on the measured data associated with the current operation of the work machine.

Once the target damage amount is obtained, and the current damage rate is determined, computer 206 may evaluate a residual of the current damage rate (Step 1215). A residual represents a degree to which the target damage rate (determined above) is not satisfied. In one embodiment, computer 206 may determine the current residual of the current damage rate by calculating a damage factor residual based upon the target damage rate. The target damage factor residual reflects a difference between the desired target damage rate (in this example, the $90^{th}$ percentile) and the actual damage rate determined by computer 206. It may be expected that some small amount of residual may exist, as any externally applied load history may not exactly give rise to the target damage rate (in this example, the $90^{th}$ percentile).

Once the current residual determined, computer 206 may collect a previously stored residual from a memory device within work machine 100, such as database 208 (Step 1220). The previous residual corresponds to a residual that was previously determined by computer 206 based on a previous operation similar to the current operation of work machine 100, determined in Step 1207. Also, computer 206 may previously have generated and stored in database 208 a previous load matrix associated with the previous residual.

At step 1225, computer 206 may compare the current residual with the previously stored damage residual. Based upon the comparison, computer 206 determines whether the new load history (i.e., candidate load matrix) more closely corresponds to the desired target damage rate by determining whether the current residual is less than the previous residual. If the current residual is not less than the previous residual (Step 1225; No), then computer 206 determines the previously stored residual, with its associated load history, is closer to the target severity level (such as the 90th percentile) than the newly calculated residual with its load history (i.e., the candidate load matrix). Accordingly, computer 206 flushes the current residual and candidate matrix (1245), and the may return to step 1205 to monitor the next operation.

If, however the current residual is less than the previous residual (Step 1225; Yes), computer 206 may determine the newly calculated-residual with its associated new load history (i.e., candidate load matrix), is closer to the target severity level (such as the 90th percentile) than the previously stored residual with its associated load history (i.e., previously stored load matrix). Accordingly, computer 206 replaces the previously stored residual with the current residual, and the load history associated with the previous residual (i.e., previous load matrix) is replaced with the current load history (i.e., candidate load matrix) in database 208 (Step 1250). In this manner, health and usage monitoring system 200 may continuously monitor for a load history that most closely matches the desired load severity. The process may return to Step 1205 to monitor for the next operation.

Although in the example described, the desired severity level was the $90^{th}$ percentile, it is contemplated that the disclosed embodiments may store the load history for a classified operation at any desired percentile. In one example, computer 206 is configured to execute software that stores the load histories for each operation at the lifetime maximum (i.e., 100th percentile). Alternatively, computer 206 may store load histories for sets of severity levels, such as the 90th, 50th, and 10th percentile for each component and each operation. Storing the load history between time $t_1$ and $t_2$ for each operation at a desired severity level provides a manageable amount of data for analysis, thus reducing the amount of memory space used to store load history data. Accordingly, a user or software executed process may access database 208 to view and/or analyze the load histories for each desired severity level and thus obtain operation profiles of work machine 100.

Figure 13:
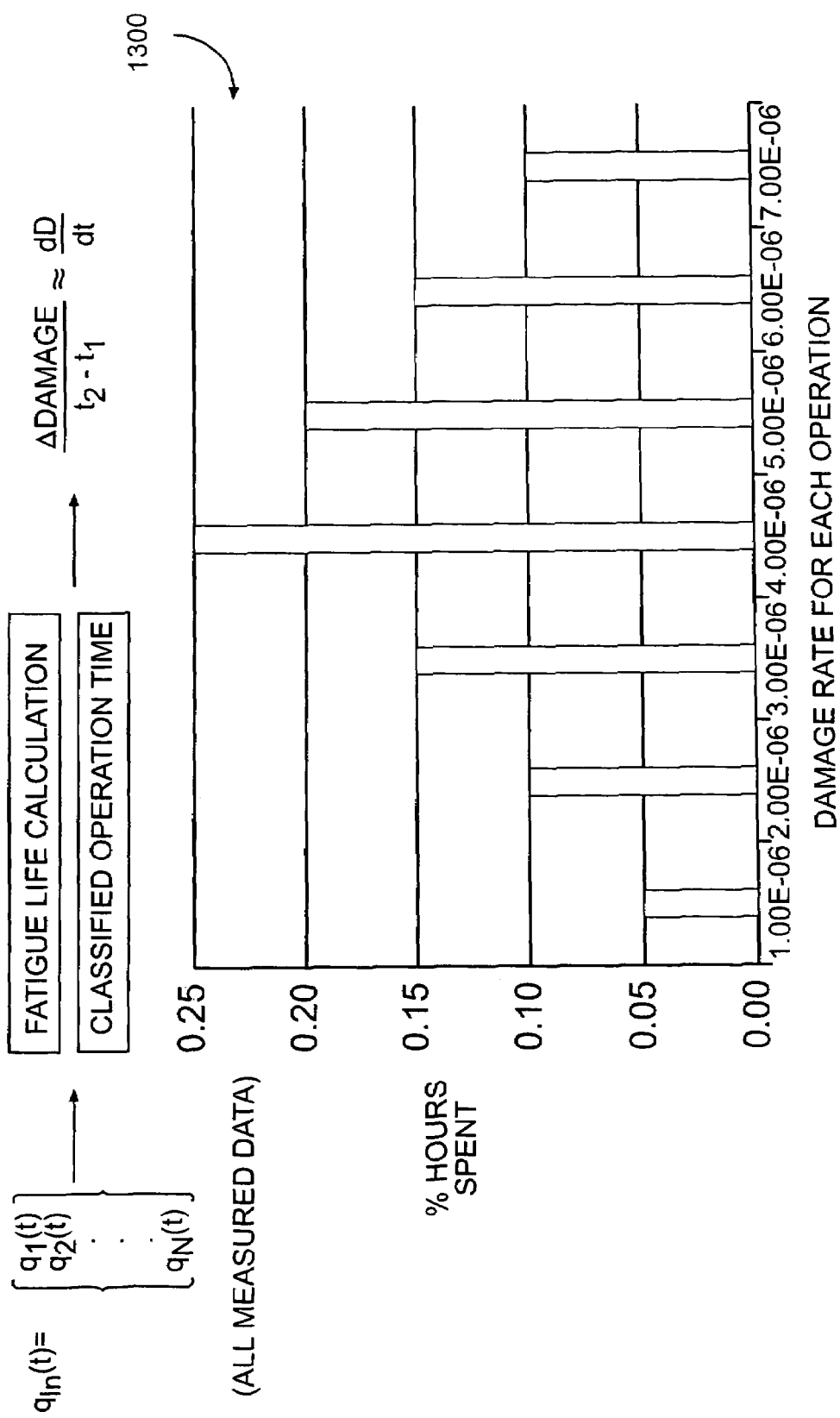
FIG. 13 is a block diagram of an exemplary damage rate histogram consistent with certain disclosed embodiments.

Additionally, as mentioned above, information for generating a damage rate histogram may be stored in vehicle database 208 and made accessible to a user or computer system, such as computer 206 or an off-board computer system. For example, FIG. 13 shows a damage rate histogram 1300 for an exemplary operation of work machine 100. In this exemplary embodiment, histogram 900 may be developed to represent the damage rate over the lifetime of work machine 100 for the single classified operation, such as the digging operation.

As shown in FIG. 13, the x-axis of histogram 1300 may represent damage rates with increasing severity. The y-axis may represent percentage of hours spent at each damage rate while performing the respective classified operation. Computer 206, or other system components of work machine 100, may collect the information for generating the histogram. For example, sensors 210-228 may measure and collect certain types of data, such as strain data values.

Computer 206 may use the collected data to perform the fatigue life calculations described above consistent with certain disclosed embodiments. Therefore, computer 206 may determine the length of time for a single classified operation time interval (e.g., $t_1<t<t_2$). The change in determined damage may be divided by the time period, and the quotient will determine the damage rates, which computer 206 (or another computer-based system) formats into data that is provided to a display device for display. Computer 206 may use the result of the calculated weighted integral damage rate, determined using the target damage equation described above, to update the histogram 1300. After the histogram has been populated, a damage rate of any severity level (e.g., 10th, 50th, 90th, or 100th percentile) for any operation may be obtained for use in selecting the load history of corresponding severity.

In another embodiment, computer 206 may store information in database 208 reflecting the detection of a crack or loosely fitted part associated with a component of work machine 100. As explained above, methods and systems of the disclosed embodiments may detect a crack based on a comparison/cross-plot of calculated and measured strain for the component. For instance, computer 206 may consider the slope and correlation coefficient derived from a cross-plot and least-squares linear fit of calculated vs. measured strain for any given strain channel of the component. Computer 206 may use this information as an indication of crack initiation in the given component and provide a warning to a user or other computer system. Thus, a user may be warned of pending cracks in a machine component. For example, computer 206 may provide a warning of crack initiation for a given component to the operator or owner of work machine 100, via a display device or warning panel. Alternatively, or additionally, computer 206 may provide the warning to a software process executing in another computer system, such as an ECM controlling engine operations. In response to the warning, the computer system may perform a process to avoid further damage to the component, such as reducing engine idle speed, stopping the engine, etc.

It should be noted that the information contained in vehicle database 208 may be used to extrapolate accumulated damage associated with one or more components of work machine 100, or of work machine 100 itself, even if one or more of sensors 210-228 have ceased to function. For example, consider a situation where all of the instrumented pins and wireless strain gages implemented on machine 100 have ceased to function, and only vehicle speed, cylinder displacement, and cylinder force sensors remain operational. Computer 206 may still be able to determine the classified operation of work machine 100 based on the available parameters obtained from the operational sensors. For instance, during an particular operation, computer 206 may match the average power expended by the cylinders to the appropriate "damage-rate bin" in the damage rate histogram 1300 for that operation, based upon previous correlations made by computer 206. In this manner, computer 206 may estimate an additional amount of damage without any fatigue life calculations based upon strain, either calculated or measured.

Figure 14:
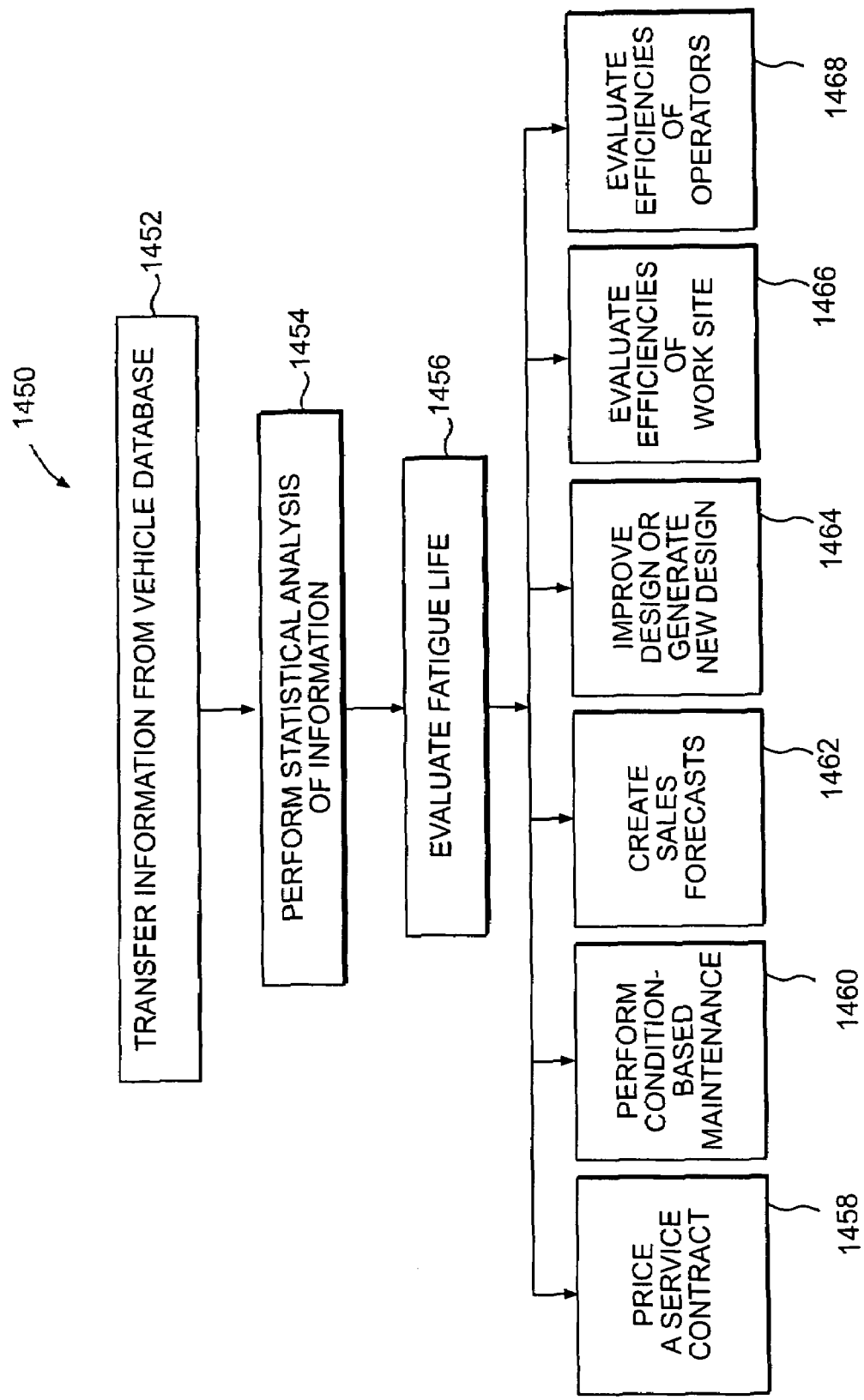
FIG. 14 is a flow chart of an exemplary data analysis process consistent with certain disclosed embodiments.
Figure 10:
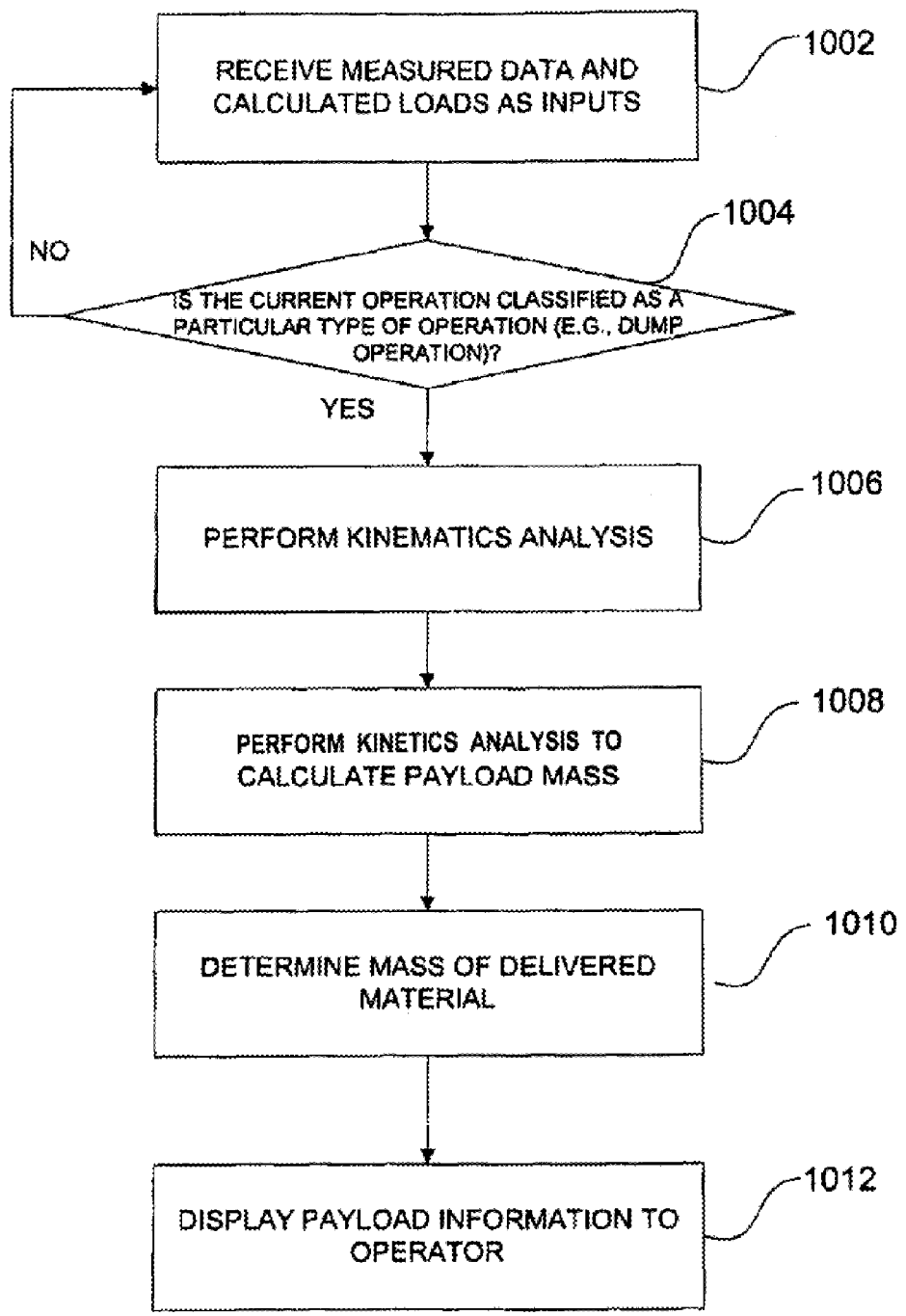
Figure 12:
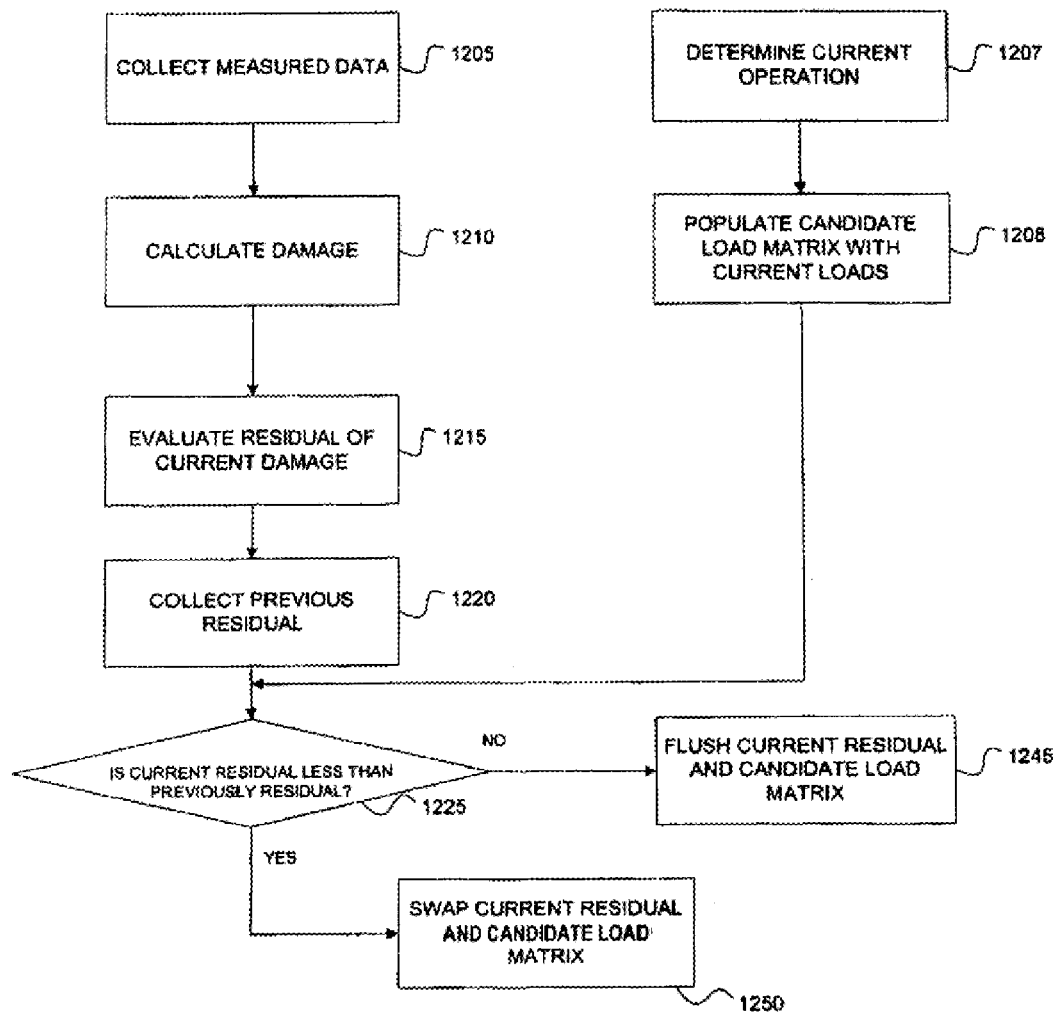

As explained, methods and systems consistent with the disclosed embodiments enable a user or off-board system to collect health and usage information from work machine 100. FIG. 14 shows a flow chart 1450 of an exemplary data analysis process consistent with certain embodiments. In one example, computer 206, or another computer system, may transfer information from vehicle database 208 to an off-board system, such as an external database (Step 1452).

In one embodiment, the off-board system may be configured to receive and analyze information from a plurality of work machines.

At step 1454, the off-board system may perform statistical analysis of the information. For example, when information from multiple work machines has been downloaded to an off-board database, the off-board system, a user, or another computer system, may access the database to compare and analyze the machine information for structural integrity of one or more components of work machine 100, and the other machines. The information may be analyzed for, among other things, abusive use of the analyzed machine. Further, the off-board system may rank the remaining fatigue life of one or more work machines (Step 1456).

Steps 1458 to 1468 show a number of possible uses of the information downloaded from work machine 100. For example, at step 1458, a service contract may be priced based on the fatigue life evaluated at step 1456. The service contract may be priced to take into account the remaining fatigue life, as well as any rough handling due to heavy loading that may have been applied to work machine 100.

At step 1460, the data may be screened for condition-based maintenance that should be performed. This may include evaluating the health related data for work machine 100 to determine which components are most in need of maintenance based upon their remaining life or their condition. Accordingly, components having a short remaining fatigue life may be maintained or replaced to ensure efficient and continuous operation of work machine 100.

At a step 1462, sales forecasts may be created by dealers based upon the remaining fatigue life of the work machines. Accordingly, dealers may be able to predict the future needs of a customer and thereby create sales forecasts. At a step 1464, engineers may design or generate new designs for work machine 100 based upon the evaluated fatigue life and the information obtained from work machine 100. For example, using the information obtained from work machine I 00, engineers may be able to remove excess material from components or areas of components that may not receive high stress. In one exemplary embodiment, new designs may be based upon the downloaded health information.

In step 1466, efficiencies of a work site including one or more work machines that include health and usage monitoring system 200 may be evaluated. In one exemplary embodiment, an off-board system may review and analyze the amount of time a work machine, or a set of work machine, performs a specific operation. For example, if an inordinate amount of time is spent roading without a load, then that efficiency may be noted and corrected to create a more efficient work site.

In step 1468, the efficiency of specific operators may be evaluated using the information obtained from vehicle database 208. For example, the information may indicate that one operator is more efficient than another operator in performing certain operations of a type of work machine at a work site. Using such information, work site managers may be able to recommend additional training or additional operators to maintain an efficient work site. Other uses for the information obtained from health and usage monitoring system 200 may also be available.

Although health and usage monitoring system 200 is described with reference to a work machine, it should be noted that methods and systems consistent with the disclosed embodiments may be used with structures and components other than work machines. For example, health and usage monitoring system 200 may be used to monitor any structural system subject to fatigue life. In some embodiments, health and usage monitoring system 200 may be used to monitor any structural system that may be used to perform a plurality of operations. Some examples of other structures that may incorporate health and usage monitoring system 200 disclosed herein may include civil structures, aircraft, and automobiles. Other structures may equally benefit from the system described herein.

Methods and systems consistent with the disclosed embodiments provide useful information that allows operators, user, and computer systems to assess the health of a work machine and perform further analysis based on this information. For instance, because health and usage monitoring system 200 gathers data related to structural mechanics and estimates structural life in near real-time, it may be used to monitor the structural integrity of a structure, such as, for example a work machine, throughout the structure's lifespan. Moreover, as mentioned above, health and usage monitoring system 200 also may be useful for providing information to assist the design, manufacture, operation, resale, and repair of components and work machines. For example, over time, the information obtained by health and usage monitoring system 200 may be used to more efficiently design and more accurately analyze components of a work machine. The structures may then be redesigned and manufactured with, for example, different materials and dimensions that may be lighter, less expensive, stronger, etc., while still providing acceptable performance in the field.

It will be apparent to those skilled in the art that various modifications and variations can be made in the disclosed embodiments without departing from the scope of the invention. Other embodiments of the disclosed embodiments will be apparent to those skilled in the art from consideration of the specification and practice of the disclosed embodiment. For example, the process steps shown in the disclosed figures may be performed in different order, and are not limited to the sequences illustrated therein. Also, additional or fewer process steps may be implemented during these processes. Further, although the disclosed embodiments describe computer 206 executing software associated with neural networks to perform specific processes, methods and systems consistent with the disclosed embodiments may allow computer 206 to request another system to execute this software and report its results to computer 206. Further, computer 206 may download neural network software from off-board systems prior to, or subsequent to, the network being trained. In another embodiment, the payload determination process may be performed for operations other than dump operations. For instance, computer 206 may perform payload determination processes when work machine 100 is roading with a load, etc.

Further, an off-board system, as the term is used herein, may represent a system that is located remote from work machine 100. An off-board system may be a system that connects to the work machines through wireline or wireless data links. Further, an off-board system may be a computer system including known computing components, such as one or more processors, software, display, and interface devices that operate collectively to perform one or more processes. Alternatively, or additionally, an off-board system may include one or more communication devices that facilitate the transmission of data to and from the work machines. In certain embodiments, an off-board system may be another work machine remotely located from work machine 100.

Additionally, although the disclosed embodiments are described as being associated with data and software programs stored in memory and other storage mediums, one skilled in the art will appreciate that these embodiments may also be stored on or read from other types of computer-readable media, such as secondary storage devices, like hard disks, floppy disks, optical storage devices, DVDs, or CD-ROM; a carrier wave from a communication link or network, such as the Internet; or other forms of RAM or ROM. It is intended that the disclosed embodiments and described examples be considered as exemplary only, with a true scope of the invention being indicated by the following claims and their equivalents.

What is claimed is:

1. A method of estimating fatigue life of a structure, comprising:
    determining strain on the structure using a plurality of gauges positioned on the structure;
    detecting a parameter of the structure with a plurality of sensors positioned on the structure;
    converting the detected parameter and the determined strain to proportional loads acting on the structure;
    transforming the proportional loads to coordinate system data associated with the structure; and
    estimating a fatigue life of the structure based on the coordinate system data.

2. The method of claim 1, including determining unmeasured loads acting on the structure based on the detected parameter.

3. The method of claim 2, wherein determining unmeasured loads is accomplished using a neural network.

4. The method of claim 3, wherein the neural network is processed by a computer positioned in a machine including the structure.

5. The method of claim 2, wherein transforming the proportional loads includes:
    generating a free-body diagram of the structure based on determined strain, the determined unmeasured loads, and the proportional loads.

6. The method of claim 1, including calculating strain at a first location on the structure that does not include a gauge based on the transformed proportional loads.

7. The method of claim 6, including comparing the calculated strain at the first location and the determined strain to determine whether fatigue damage is present in the structure.

8. The method of claim 6, wherein calculating strain at the first location includes calculating the strain based on an influence coefficient matrix including data reflecting a strain response at a number of chosen locations of the structure under the influence of a particular unit load.

9. The method of claim 1, wherein estimating a fatigue life of the structure includes:
    determining the fatigue life of the structure for a first predetermined time during a life of the structure; and
    determining the fatigue life of the structure for a second predetermined time during the life of the structure, the second predetermined time being subsequent to the first predetermined time.

10. The method of claim 9, wherein the second predetermined time is associated with a time period when the age of the structure approaches a time period associated with an originally estimated fatigue life for the structure, and wherein determining the fatigue life during for second predetermined time includes employing Bayes' theorem to estimate the fatigue life of the structure.

11. The method of claim 1, including analyzing the estimated fatigue life to determine at least one of a value of the structure, a price of a service contract associated with the structure, and a suggested time period to perform maintenance on the structure.

12. The method of claim 1, wherein estimating the fatigue life is performed by a computer located in a machine in real-time during a current operation of the machine.

13. A system for estimating a remaining fatigue life of a structure, comprising:
- a structure positioned on a machine performing operations;
- gauges positioned on the structure and configured to measure strain on the structure during operations of the machine;
- sensors positioned on the structure and configured to detect a parameter associated with the structure; and
- a computer located on the machine and configured to:
  - determine strain on the structure based on the measured strain,
  - convert the detected parameter and the determined strain to proportional loads acting on the structure,
  - transform the proportional loads to a coordinate system data associated with the structure, and
  - estimate a fatigue life of the structure based on the coordinate system data.

14. The system of claim 13, wherein the computer is configured to determine unmeasured loads acting on the structure based on the detected parameter.

15. The system of claim 14, wherein the computer uses a neural network to determine the unmeasured loads based on the detected parameter.

16. The system of claim 15, wherein the computer transforms the proportional loads to a coordinate system data associated with the structure by analyzing the structure as a free-body diagram using the determined strain, the determined unmeasured loads, and the proportional loads.

17. The system of claim 13, wherein the computer calculates strain at a first location on the structure that does not include a gauge based on the transformed proportional loads.

18. The system of claim 17, wherein the computer compares the calculated strain at the first location and the determined strain to determine whether fatigue damage is present in the structure.

19. The system of claim 17, wherein the computer calculates strain at the first location by calculating the strain based on an influence coefficient matrix including data reflecting a strain response at a number of chosen locations of the structure under the influence of a particular unit load.

20. The system of claim 13, wherein the computer estimates the fatigue life of the structure by determining the fatigue life of the structure for a first predetermined time during a life of the structure, and determining the fatigue life of the structure for a second predetermined time during the life of the structure, the second predetermined time being subsequent to the first predetermined time.

21. The system of claim 20, wherein the second predetermined time is associated with a time period when the age of the structure approaches a time period associated with an originally estimated fatigue life for the structure, and wherein the computer uses Bayes' theorem in order to estimate the fatigue life of the structure for the second predetermined time.

\* \* \* \* \*

UNITED STATES PATENT AND TRADEMARK OFFICE
CERTIFICATE OF CORRECTION

PATENT NO. : 7,328,625 B2
APPLICATION NO. : 11/227157
DATED : February 12, 2008
INVENTOR(S) : Sundermeyer et al.

It is certified that error appears in the above-identified patent and that said Letters Patent is hereby corrected as shown below:

Please correct the Drawings as follows (applicant errors):
Sheet 10 of 14, in FIG. 10, delete "KNETICS" and insert -- KINETICS --. As shown in the attached page.

Sheet 12 of 14, in FIG. 12, delete "CANDIATE" and insert -- CANDIDATE --. As shown in the attached page.

Please correct the Specification as follows (PTO errors):
Column 9, line 44, delete "that-transfer" and insert -- that transfer --.

Column 18, line 8, delete "$\varepsilon_f$" and insert -- $\varepsilon_f'$ --.

Column 22, line 64, delete "ti" and insert -- $t_1$, --.

Column 23, line 5, delete "processes-described" and insert -- processes described --.

Column 23, line 58, delete "-for" and insert -- for --.

Column 23, line 63, delete "I 00." and insert -- 100. --.

Column 24, line 20, delete "1 00" and insert -- 100 --.

Column 24, line 53, delete "10," and insert -- 110, --.

Column 30, line 19, delete "calculated-residual" and insert -- calculated residual --.

UNITED STATES PATENT AND TRADEMARK OFFICE
CERTIFICATE OF CORRECTION

| | |
|---|---|
| PATENT NO. | : 7,328,625 B2 |
| APPLICATION NO. | : 11/227157 |
| DATED | : February 12, 2008 |
| INVENTOR(S) | : Sundermeyer et al. |

It is certified that error appears in the above-identified patent and that said Letters Patent is hereby corrected as shown below:

Column 32, line 38, delete "I 00," and insert -- 100, --.

Signed and Sealed this

Twenty-fifth Day of November, 2008

JON W. DUDAS
*Director of the United States Patent and Trademark Office*